(12) United States Patent
Elgebaly et al.

(10) Patent No.: US 8,288,350 B2
(45) Date of Patent: Oct. 16, 2012

(54) METHODS TO PREVENT AND TREAT DISEASES

(75) Inventors: Salwa A. Elgebaly, Annapolis, MD (US); Elliott Schiffmann, Chevy Chase, MD (US)

(73) Assignee: Nour Heart, Inc., Germantown, MD (US)

( * ) Notice: Subject to any disclaimer, the term of this patent is extended or adjusted under 35 U.S.C. 154(b) by 0 days.

(21) Appl. No.: 13/111,571

(22) Filed: May 19, 2011

(65) Prior Publication Data

US 2011/0245149 A1    Oct. 6, 2011

Related U.S. Application Data

(63) Continuation of application No. 11/693,289, filed on Mar. 29, 2007, now abandoned.

(60) Provisional application No. 60/876,457, filed on Dec. 20, 2006, provisional application No. 60/846,685, filed on Sep. 21, 2006, provisional application No. 60/835,748, filed on Aug. 3, 2006, provisional application No. 60/818,806, filed on Jul. 5, 2006.

(51) Int. Cl.
*A61K 38/04* (2006.01)
*A61K 38/13* (2006.01)
*A61K 38/00* (2006.01)

(52) U.S. Cl. ........ 514/21.4; 514/1.1; 514/2.3; 514/12.2; 514/18.3; 514/20.5

(58) Field of Classification Search .................. None
See application file for complete search history.

(56) References Cited

U.S. PATENT DOCUMENTS

| | | | |
|---|---|---|---|
| 4,793,998 | A | 12/1988 | Murthy et al. |
| 5,091,404 | A | 2/1992 | Elgebaly |
| 5,270,163 | A | 12/1993 | Gold et al. |
| 5,403,914 | A | 4/1995 | Elgebaly |
| 5,504,013 | A | 4/1996 | Senior |
| 5,606,027 | A | 2/1997 | Elgebaly |
| 5,622,871 | A | 4/1997 | May et al. |
| 6,235,241 | B1 | 5/2001 | Catt et al. |
| 6,399,398 | B1 | 6/2002 | Cunningham et al. |
| 6,670,138 | B2 | 12/2003 | Gonzalez-Zulueta et al. |
| 2004/0261140 | A1* | 12/2004 | Benson .......................... 800/18 |
| 2005/0137481 | A1 | 6/2005 | Sheard et al. |

FOREIGN PATENT DOCUMENTS

| | | |
|---|---|---|
| WO | 91/19813 | 12/1991 |
| WO | 92/05285 | 4/1992 |
| WO | 92/14843 | 9/1992 |
| WO | 03/074069 | 9/2003 |

OTHER PUBLICATIONS

Creatine from MedlinePlus (www.nlm.nih.gov/medlineplus/druginfo/natural/873.html, pp. 1-4. Accessed Nov. 8, 2011.*

Beattie M. S., Trends in Molecular Medicine, 2004, vol. 19, No. 12, pp. 580-583.
Yamazaki et al., European Journal of Pharmacology, 2001, vol. 413, pp. 173-178.
O'Flaherthy et al., The Journal of Immunology, 1978, vol. 120, No. 4, pp. 1326-1332.
Le et al., Trends in Immunology, 2002, vol. 23, No. 11, pp. 541-548.
Lutsenko et al., Proc. Natl. Acad. Sci., 1998, vol. 95, pp. 6004-6009.
Koehler et al., Proc. Natl. Acad. Sci., 1999, vol. 96, pp. 2141-2146.
Alpert, J.S. et al., "Myocardial Infarction Redefined—A Consensus Document of The Joint European Society of Cardiology/American College of Cardiology Committee for the Redefinition of Myocardial Infarction," J. Am. Coll. Cardiol. 2000; 36; 959-69.
Boersma, E. et al., "Platelet glycoprotein llb/lla inhibitors in acute coronary syndromes; a meta-analysis of all major randomized clinical trials," Lancet 2002:359: 189-98.
Brennan, M.L. et al., "Prognostic Value of Myeloperoxidases in Patients with Chest Pain," N. Engl. J. Med. 2003: 349: 1595-604.
Christenson, R.H. et al., "Characteristics of an Albumin Cobalt Binding Test for Assessment of Acute Coronary Syndrome Patients: A Multicenter Study," Clin. Chem. 2001; 47:464-470.
Christenson, R.H. and Azzazy, H.M.E., "Biochemical markers of acute coronary syndromes," Clin. Chem., 44, 1855-64, 1998.
Danne, O. et al., "Prognostic Implications of Elevated Whole Blood Choline Levels in Acute Coronary Syndrome," Am. J. Cardiol. 2003; 91: 1060-7.
De Lemos, J.A. et al., "The Prognostic Value of Serum Myoglobin in Patients with Non-ST-Segment Elevation Acute Coronary Syndromes," J. Am. Coll. Cardiol. 2002; 40: 238-44.
Doherty, D.E. et al., Human Monocyte Adherence: A Primary Effect of Chemotactic Factors on the Monocyte to Stimulate Adherence to Human Endothelium, J. Immunol. 138(6), 1762-1771, 1987.
Elgebaly, S.A. et al., "Cardiac Derived Neutrophil Chemotactic Factors; Preliminary Biochemical Characterization," J. Mol. Cell Cardiol., 21:585-593, 1989.
Elgebaly Y, S.A. et al., "Cyclocreatine Inhibits the Production of Nutrophil Chemotactic Factors from Isolated hearts,"Am. J. Pathol. 137: 1233-1241, 1990.
Elgebaly Y, S.A. et al., "Cardiac derived neutrophil chemotactic factors: Detection in coronary sinus effluents of patients undergoing myocardial revascularization," J. Thorac. Cardiovasc. Surg., 130(5): 952-959, 1992.
Elgebaly, S.A. et al., "Evidence of Cardiac Inflammation After Open Heart Operations," Ann. Thorac. Surg., 57: 391-396, 1994.
Joyce, "Amplification, mutation and selection of catalytic RNA" (1980) Gene 82.83-87.
Kleinfeld, A. M. et al., "Increases in Serum Unbound Free Fatty Acid Levels Following Coronary Angioplasty," Am. J. Cardiol., 1996, 78:1350-4.
Lucchesi, B.R. et al., "Leukocytes and Ischemia-induced Myocardial Injury," Annu. Rev. Pharmacol. Toxicol., 26:201-224, 1986.
Newby, L.K. et al., "Bedside Multimarker Testing fr Risk Stratification in Chest Pain Units," Circulation, 2001, 103:1832-7.

(Continued)

*Primary Examiner* — Julie Ha
(74) *Attorney, Agent, or Firm* — Latimer IP Law, LLC

(57) ABSTRACT

Methods and compositions that can treat a variety of tissue injuries and infections are provided. Tissue-derived leukocyte chemotactic factors are rapidly released after injury to mammalian tissue and can act as the initial signal leading to the initiation and amplification of acute and chronic inflammation associated with injury and infection. The present invention generally provides methods and compositions to prevent and treat injury of cells, tissue, or organs by blocking or inhibiting the release of leukocyte chemotactic factors, by administering certain effective compositions to the tissue.

13 Claims, 4 Drawing Sheets

OTHER PUBLICATIONS

Szostak et al., "In vitro selection of RNA molecules that bind specific ligands," (1990) Nature 346:818-822.

Tuerk et al., "Systematic Evolution of Ligands by Exponential Enrichment: RNA Ligands to Bacteriophage T4 DNA Polymerase" (1990) Science 249:505-510.

Yamamoto, Yuri et al., "Inhibitory Effects of Spinorphin, a Novel Endogenous Regulator, on Chemotaxis, O2 Generation, and Exoytosis byN-Formylmethionyl-leucyl-phenylalanine (FMLP)-Stimulated Neutrophils," Biochemical. Pharmacology, 54; 695-701, 1997.

Trueba et al. (J. Bacteriology 1992 vol. 174, p. 4761-4768).

Definition of derivative (analog) from http://cancerweb.ncl.ac.uk/cgi-bin/omd?query=derivative, pp. 1-5. Accessed Jul. 7, 2005.

Talanian RV, Brady KD, Cryns VL, "Caspases as targets for anti-inflammaotry and anti-apoptotic drug discovery," Medicinal Chemistry, 2000, 43(18): 3351-3371.

Liang TS, Gao J-J, Fatemi O, Lavigne M, Leto TL, Murphy PM, "The endogenous opiod spinorphin blocks fMet-Leu-Phe-Induced neutrophil chemotaxis by acting as a specific antagonist at the N-formylpeptide receptor subtype FPR," The journal of Immunology, 2001, 167: 6609-6614.

Yamamoto Y, Ono H, Ueda A, Shimamura M, Nishimura K, Hazato T, "Spinorphin as an endogenous inhibitors of enkephalin-degrading enzymes: roles in pain and inflammation," Current Protein and Peptide Science, 2002, 3: 587-599.

\* cited by examiner

METHODS TO PREVENT AND TREAT DISEASES

CROSS-REFERENCE TO RELATED APPLICATIONS

This application is a continuation of U.S. patent application Ser. No. 11/693,289, filed 29 Mar. 2007, which relies on the disclosures of and claims the benefit of the filing dates of U.S. provisional patent application No. 60/818,806, filed 5 Jul. 2006, U.S. provisional patent application No. 60/835,748, filed 3 Aug. 2006, U.S. provisional patent application No. 60/846,685, filed 21 Sep. 2006, and U.S. provisional patent application No. 60/876,457, filed 20 Dec. 2007, the entire disclosures of all of which are hereby incorporated herein by reference.

BACKGROUND OF THE INVENTION

1. Field of the Invention

The present invention relates to the field of human and veterinarian medicine. More specifically, the invention relates to prevention and treatment of tissue and organ injury and infection in animals, such as mammals.

2. Discussion of Related Art

Tissue-derived leukocyte chemotactic factors (LCFs) are a group of approximately 3 KDa peptides that are rapidly released by local tissues (within about 5 minutes) in response to injury induced by, for example, chemical agents, such as hydrogen peroxide, sodium hydroxide, citric acid, and alcohol. They are also release in response to physical trauma, such as: scraping; vitamin A deficiency; ultraviolet exposure; ischemia; shear stress; viral infection; and endotoxin treatments. Tissue-derived LCFs were isolated from injured tissues both in vitro using organ culture and cell culture, as well in vivo using animal models and patients with various diseases. Unique tissue-specific LCFs are known to be released by corneal, conjunctival, retinal, heart, coronary arteries, vessels, urinary bladder, brain, spinal cord, and gastric tissues in response to injury.

LCFs are inflammatory mediators that (a) recruit leukocytes from the circulation into sites of infection or tissue injury, (b) stimulate the secretion of adhesion molecules by leukocytes and vascular endothelial cells and accordingly increase the adhesion of cells to the site of injury, and (c) activate leukocytes and vascular endothelial cells to release chemokines, cytokines, and toxic agents such as oxygen metabolites and digestive enzymes.

Various groups have studied LCFs and the inflammation process. For example, U.S. Pat. No. 5,403,914 (herein incorporated by reference) discloses the release of a leukocyte chemotactic factor (LCF) from cardiac tissue in response to injury. The LCF represents the initial signal that recruits leukocytes to the injured tissue. Furthermore, U.S. Pat. No. 5,091,404 (herein incorporated by reference) discloses a system using cyclocreatine to preserve and/or restore the physiological functionality of myocardial tissue subject to ischemia, and particularly tissue subject to reperfusion. The system imparts to the cardiac tissue the ability to sustain high levels of adenosine triphosphate or at least delay the depletion of adenosine triphosphate (ATP) during total ischemia. It delays the development of acidosis and enhances the prompt recovery of tissue function, such as contractility, in such muscle tissue during and following post-ischemic reperfusion.

An inflammatory reaction within tissue is generally characterized by leukocyte infiltration, edema, redness, pain, neovascularization (in advanced cases), and finally impairment of function. Neutrophils are the major inflammatory cells in acute inflammation, while mononuclear cells are the major cells in chronic inflammation. Acute and chronic inflammation are documented to occur after diverse types of tissue injury. When inflammation is controlled, it provides a central host defense. Uncontrolled inflammation, on the other hand, can cause potentially destructive biological responses.

Leukocyte-mediated cell injury is believed to be a major mechanism of tissue injury in acute and chronic inflammation. Leukocytes release cytotoxic compounds, such as reactive oxygen metabolites (e.g., hydrogen peroxide, superoxide anion, and hydroxyl radicals) and digestive proteolytic enzymes (e.g., collagenase and elastase). In the case of reperfusion after ischemia, neutrophils could also be deleterious to injured tissues because of their large size. Neutrophils can plug tissue capillaries during reperfusion resulting in what is known as the "no-reflow" phenomenon with resultant impaired perfusion. Furthermore, activated neutrophils induce extended cell injury during "early reperfusion" after ischemia.

There is a need in the art to provide compositions and methods to inhibit both tissue inflammation and tissue apoptosis. For treatment and prevention of injuries to organs, there is a need to provide compositions and methods to inhibit cytokine storms and organ apoptosis. There is furthermore a need to improve treatment of tissue infections. For example, a current treatment for anthrax infection involves the use of several different antibiotics, used in combination with vaccines. New therapeutic approaches are necessary to better protect anthrax-infected patients from vasculitis, vascular and tissue apoptosis, edema, as well as tissue damage. There is a need in the art to improve treatment of infections in general.

Vaccines and viral medications are the two most common approaches generally used to prevent and treat viral infections, but neither can control the excessive host inflammatory response including cytokine storms, which occur secondary to Avian viral influenza infections and can cause death.

What is particularly needed are methods and compositions that can treat a wide variety of tissue injuries across different mammalian tissues as well as different types, severities, and durations of tissue injuries.

SUMMARY OF THE INVENTION

Tissue-derived leukocyte chemotactic factors are rapidly released after injury to mammalian tissue and can act as the initial signal leading to the initiation and amplification of acute and chronic inflammation associated with injury and infection. The present invention generally provides methods and compositions to prevent and treat tissue injury by blocking or inhibiting the release of leukocyte chemotactic factors. In this invention, by "injury" of mammalian cells, tissue, or organs is meant all possible sources of damage or harm to the structure or function of such cells, tissue, or organs.

In a first aspect, the invention provides a method of treating animal tissue, such as mammalian tissue, that has been subject to injury. In general, the method can comprise: administering to the animal at least one tissue-protective agent in an amount that is effective for imparting to a tissue an anti-inflammatory response, an anti-apoptotic response, or both anti-inflammatory and anti-apoptotic responses.

In another aspect, the invention provides a tissue-protective agent. The tissue-protective agent can comprise one or more agents having the desired activity. For example, the agent can be spinorphin, tynorphin, leuhistin, nimbidin, t-Boc-Phe-D-Leu-Phe-D-Leu-Phe (SEQ ID NO:2), t-Boc-Methionyl-Leucyl-Phenylalanine (SEQ ID NO:5), Carbobenzoxy-Phe-Met, Substance P antagonist R(dextro-)PKP(dextro-)FQ(dextro-)WF(dextro-)WLL-NH$_2$ (SEQ ID NO:6), Cyclosporine H, or pentoxifylline. The tissue-protective agent can also include one or more of a variety of anti-oxidants, such as ascorbic acid or lycopene.

Among other things, the tissue-protective agent can comprise an antibody against formyl peptide receptors that can bind to formylated ligands, or an antibody against formyl peptide receptors that can bind to non-formylated ligands. The tissue-protective agent of the invention can comprise a plurality of soluble formyl peptide receptors that can bind to formylated ligands, or a plurality of soluble formyl peptide receptors that can bind to non-formylated ligands. The agent can also comprise an antibody against a tissue-derived leukocyte chemotactic factor.

The tissue-protective agent can comprise a creatine analogue, such as cyclocreatine, a salt of cyclocreatine (e.g., cyclocreatine phosphate), or other known creatine analogues or molecular entities with the same or similar function to creatine analogues.

In some embodiments relating to creatine analogues, a method of treating animal (e.g., mammalian) tissue subject to injury comprises the step of administering to the mammal a creatine analogue in an amount between 0.01 g and 0.1 g creatine analogue per kg of mammal body weight. In certain embodiments, the administered dose of creatine analogue is in the 0.03-0.08 g/kg range. In these embodiments, the creatine analogue (e.g., cyclocreatine and cyclocreatine phosphate) can reduce intracellular cAMP production in the tissue. Tissue apoptosis can be significantly reduced or eliminated.

The tissue-protective agent can comprise, among other things, a metabolite of the mitochondria of the mammalian tissue. The metabolite can be selected from acetyl L-carnitine, coenzyme Q10, glutathione, or α-lipoic acid, or other metabolites.

In preferred embodiments of the invention, the anti-inflammatory response arises from one or more actions of the tissue-protective agent. Such actions can be, among other things, delaying the depletion of adenosine triphosphate in the tissue, conserving the total adenylate pool in the tissue, buffering a decrease in the ratio of adenosine triphosphate to free adenosine diphosphate in the tissue, delaying exhaustion of high-energy phosphates in the tissue, maintaining cell-membrane integrity in the tissue, inhibiting caspase enzyme activity in the tissue, and reducing intracellular edema in the tissue.

In some embodiments, the tissue-protective agent crosses the blood-brain barrier of the animal (e.g., mammal). In certain embodiments, the agent accumulates in nerve tissue of the animal. In some embodiments, the agent reduces lactic acidosis in the tissue. The agent can also reduce the level of malondialdehyde in the tissue.

The tissue can be from any animal. Thus, it can be human tissue (or tissue of any other mammal) and can be treated in vivo or in vitro.

The tissue-protective agent can be used in methods of treating. Accordingly, the tissue-protective agent can be administered prophylactically, therapeutically during injury, or post-injury for continued therapy or prophylactically against recurrence. The agent can be administered by any suitable means, including, but not limited to, injection, orally, topically, by inhalation, or by other means. In some embodiments, the injury to be prevented or treated is related to ischemia. In other embodiments, the injury is related to infection. In certain embodiments, methods further comprise administering to the animal an additional agent that is capable of generating nitric oxide in vivo.

In accordance with the above disclosure, in another aspect, the present invention provides compositions for treating animal tissue subject to injury. A preferred composition comprises (i) at least one anti-inflammatory agent and (ii) at least one anti-apoptotic agent, where the anti-inflammatory agent is capable of inhibiting a tissue-derived leukocyte chemotactic factor. In some compositions of the invention, the anti-inflammatory agent comprises an antagonist of a tissue-derived leukocyte chemotactic factor.

The identity of the anti-inflammatory agent is not limited. For example, it can be an anti-oxidant, enzyme (such as a deformylase), enzyme inhibitor, antibiotic, inhibitor of the bacterial formyl peptide chemoattractant, including but not limited to deformylase enzymes, and endogenous inhibitors of tissue-derived leukocyte chemotactic factors. The enzyme inhibitor can be, for example, L-histidine or trasylol. In certain particular embodiments, the anti-inflammatory agent can comprise the antagonist spinorphin, leuhistin, or in some embodiments, both spinorphin and leuhistin. The anti-inflammatory agent of the composition can include the antagonist tynorphin. In some embodiments, the anti-inflammatory agent can comprise one or more agents selected from the group consisting of t-Boc-Phe-Leu-Phe-Leu-Phe (SEQ ID NO:2), cyclosporine H, pentoxifylline, Carbobenzoxy-Phe-Met, and Substance P antagonist R (dextro-)PKP(dextro-)FQ(dextro-)WF(dextro-)WLL-NH$_2$ (SEQ ID NO:6).

According to some embodiments, the anti-inflammatory agent comprises a plurality of soluble formyl peptide receptors that can bind to formylated ligands, or a plurality of soluble formyl peptide receptors that can bind to non-formylated ligands. In other embodiments, the anti-inflammatory agent comprises an antibody against formyl peptide receptors that can bind to formylated ligands, or an antibody against formyl peptide receptors that can bind to non-formylated ligands. In certain preferred embodiments, the anti-inflammatory comprises an antibody against a tissue-derived leukocyte chemotactic factor.

In some embodiments, the composition includes an anti-apoptotic agent comprising a creatine analogue. The creatine analogue can be cyclocreatine, a salt of cyclocreatine (e.g., cyclocreatine phosphate), or other known creatine analogues or molecular entities with the same or similar function to creatine analogues.

The anti-apoptotic agent of the composition can comprise a metabolite of the mitochondria. The metabolite can be selected from acetyl L-carnitine, coenzyme Q10, glutathione, α-lipoic acid or other effective metabolites.

The present invention also teaches use of the compositions described above in treatment of mammals, wherein treatment includes both prevention and therapy with respect to tissue or organ injury or infection. Some aspects of the invention therefore provide a method of using a composition to protect or treat a first tissue of a mammal, said first tissue suspected of being injured or of being susceptible to injury, comprising providing an effective amount of the composition to said first tissue, wherein the composition comprises (i) an anti-inflammatory agent and (ii) an anti-apoptotic agent, and wherein the anti-inflammatory agent is capable of inhibiting a leukocyte chemotactic factor derived from a second tissue of the mammal. The first and second tissues can be, but are not necessarily, the same tissue. Furthermore, the invention provides for use of a compound or composition of the invention in the manufacture of a medicament, and use of the compound or composition in a method of treating.

In yet another aspect, the invention provides a method of treating injured animal tissue in a subject (patient). The method generally comprises: (a) taking a sample of a subject's tissue, which is suspected of being damaged; (b) detecting the release of at least one peptide from the tissue to indicate that the tissue is in an injured state in the patient; and (c) if the tissue is injured, administering to the subject an effective amount of a composition comprising (i) an anti-inflammatory agent and (ii) an anti-apoptotic agent, wherein the anti-inflammatory agent is capable of inhibiting a tissue-derived leukocyte chemotactic factor. Of course, due to the importance of human health, the subject is often a human. However, in some embodiments, the subject is an animal and the method relates to veterinarian treatments.

DETAILED DESCRIPTION OF EMBODIMENTS OF THE INVENTION

Figure 1:
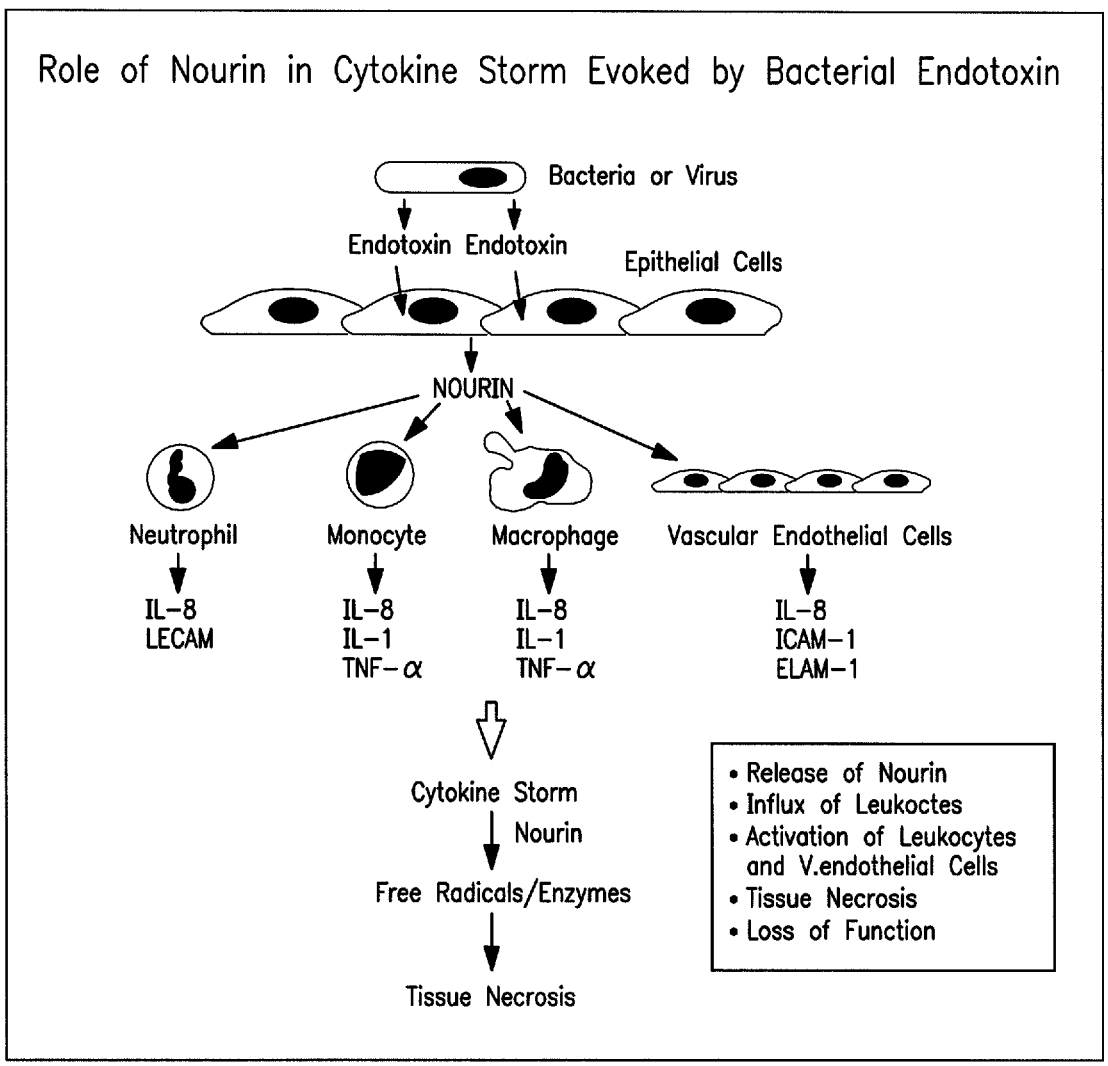
FIG. 1 is a diagram depicting the chain of events caused by a release of tissue-derived leukocyte chemotactic factors.

The following detailed description of certain embodiments of the invention is provided to give the reader a better understanding of certain details of the invention, and is not to be understood as a limitation on the scope or subject matter of the invention.

The cell response to injury depends on the kind, severity, and duration of insult. The injury may range from mild and fully reversible to severe and lethal. Clinical effects of cell injury depend on what kind of cell is affected, its prior state of health, and what sort of adaptive mechanisms are available to it. In general, the most metabolically active cells are the most susceptible to injury. For the purposes of the present disclosure, "injury" of cells, tissue, or organs is meant to encompass all possible sources of damage or harm to the structure or function of such cells, tissue, or organs, and is not to be regarded as limiting in any way.

The most common etiologic factors involved in cell injury are as follows:
Metabolic: such as (but not limited to) oxygen, glucose, cholesterol, and lipid profiles; vitamin A deficiency
Physical: such as (but not limited to) ischemia, reperfusion, cold, heat, trauma, dust, silica, radiation, ultraviolet, and electricity
Chemical agents: such as (but not limited to) acid and base solutions, hydrogen peroxide, pollutants, and solvents
Drugs: such as (but not limited to) acetaminophen, alcohol, narcotics, and glucocorticoids
Immunologic reactions: such as (but not limited to) allergies to substances and autoimmune diseases
Biologic: such as (but not limited to) viruses, bacteria, and bacterial products such as endotoxin, and parasites Ischemic injury, as an example, results from interruption in blood flow. It is well-studied, particularly in heart muscle as a result of coronary occlusion. Reversible changes are known to occur when the duration of the ischemia is short, e.g., 15 minutes and less. Irreversible changes occur if ischemia persists, resulting in cellular death.

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

Cell injury can ultimately lead to cell death. Cells can die in two ways: apoptosis and necrosis, and there are distinctive differences between necrotic and apoptotic cell death that can be observed and measured. Apoptosis is a normal, genetically controlled event which plays a critical role in removing unwanted and potentially dangerous cells, such as tumor cells and cell infected by viruses. Morphologically, apoptosis is characterized by cell shrinkage, membrane blebbing, and chromatin condensation. The apoptotic bodies are subsequently phagocytosed by surrounding cells or macrophages. Since cellular contents are not released, apoptosis does not stimulate an inflammatory response. Many agents that cause necrosis can also cause apoptosis, usually at lower doses and over longer periods of time. Examples of stimuli for apoptosis include: mild ischemia, mild radiation, viral infection, and cytokines such as tumor necrosis factor-alpha (TNF-α), lymphotoxin, and hormones such as glucocorticoids. In contrast, necrosis occurs when a cell suffers lethal injury and is characterized by swelling, rupturing of the cell, and inflammation (and associated pain). The first consequence of persisted injury (ischemia, for example) is loss of oxidative phosphorylation in mitochondria and reduction in ATP production. Reduction in ATP results in failure of the ATP-dependent sodium/potassium pumps and calcium pump that normally maintain high cell potassium and low cell sodium and calcium. Beside the massive calcium influx into the cell, the drop in ATP also results in increased glycolysis and acidosis which produces injury to lysosomal cell membranes and leakage of their powerful enzymes into cytoplasm. The leaked lysosomal enzymes will digest the cell contents, resulting in cell death. Cell necrosis in living tissue is associated with an acute inflammatory reaction.

The balance between death by apoptosis and necrosis depends not only upon the intensity of the injury but also upon the level of available intracellular ATP. A lack of ATP can cause a switch of the mode of cell death from apoptosis to necrosis.

Many diseases are the result of hypoxia (a shortage of oxygen), often due to ischemia, which is an absolute or relative shortage of blood supply to an organ or tissue. Insufficient blood supply causes tissue to become hypoxic, or, if no oxygen is supplied at all, anoxic. Hypoxia/ischemia can result in inflammation (and pain) and similarly, inflammation results in vascular damage leading to hypoxia/ischemia. Both conditions are associated with apoptosis (programmed cell death) leading to tissue degeneration and loss of function. Hypoxia and ischemia of major organs are also symptoms that occur in association with cytokine storms. A cytokine storm is a potentially fatal immune reaction comprising a positive feedback loop between cytokines and immune cells, with highly elevated levels of various cytokines.

Injury to tissue, arising due to infection, ischemic damage, or other causes as described above, can cause the release of mitochondrial and non-mitochondrial proteins. These tissue-derived proteins can be formylated or non-formylated. The released proteins can be detected in a sample taken from a subject, indicating that the subject has suffered damage. One aspect of the present invention describes methods to protect against tissue apoptosis and to treat cytokine storms associated with immune-system overload associated with infections (see FIG. 1), by inhibiting or blocking the release of these proteins, thereby decreasing the likelihood of further tissue damage that could otherwise happen.

To assist in preventing and treating tissue damage caused by oxygen variance, the present invention provides a system for causing the preservation and prompt recovery of nerve tissue function during ischemia and following post-ischemic reperfusion. Among the tissues that are treated are brain, ocular, and peripheral nerve tissues and nerve cells within these tissues. Included in this aspect is the provision for the administration of a tissue-protective agent before and/or after ischemia to preserve and restore nerve function of salvageable penumbra tissue. Particularly, the present invention involves a system that provides for a three-stage treatment of (i) prevention, (ii) immediate therapy during ischemia, and (iii) post-ischemia rehabilitation to preserve, restore, and sustain the function of nerve tissue in surgical and non-surgical patients subjected to ischemia and reperfusion.

One feature of the present invention is to provide a potent neuro-protective or neutrophic agent, such as cyclocreatine, cyclocreatine phosphate, acetyl L-carnitine, coenzyme Q10, glutathione, or α-lipoic acid, which, when administered shortly after the incidence of ischemia in the brain, the eye, and peripheral nerves will preserve the "salvageable tissue" surrounding the ischemic and necrotic areas and minimize devastating disability. In general, these compounds are provided alone or in compositions in amounts suitable for achieving these results in vivo. Administration of cyclocreatine, cyclocreatine phosphate, acetyl L-carnitine, coenzyme Q10, glutathione, and alpha lipoic acid are optionally continued post-ischemia and during reperfusion in the form of a low maintenance dose that will encourage a healthy sustained recovery of nerve tissue function. Coenzyme Q10 is a biologically active quinone with an isoprenoid side chain, related in structure to vitamin K and vitamin E.

Because ischemic cell injury in living tissue is associated with an acute inflammatory reaction, anti-apoptotic agents, such as cyclocreatine, cyclocreatine phosphate, acetyl L-carnitine, coenzyme Q10, glutathione, or α-lipoic acid, are used in combination with tissue-derived anti-inflammatory protein(s). In case of infection, antibiotics and the inhibitors of F-Met-Leu-Phe can be added including deformylases. Some of the advantages of combining anti-ischemic agents with tissue-derived anti-inflammatory agents, in accordance with some embodiments of the present invention, are as follows. The tissue-derived anti-inflammatory agent can protect the injured tissue from damage induced by inflammation during "early reperfusion" without affecting the necessary healing process. The tissue-derived anti-inflammatory agent can inhibit the release of the cytokine tumor necrosis factor-alpha from activated leukocytes and therefore further protect tissues against the initiation of apoptosis and the progression of injury from reversible to irreversible. Additionally, the tissue-derived anti-inflammatory agent can replace the immunosuppressor glucocorticoids which are known to stimulate the initiation of apoptosis in reversibly injured tissues. Further, in general, cyclocreatine, cyclocreatine phosphate, acetyl L-carnitine, coenzyme Q10, glutathione, and α-lipoic acid, or other anti-apoptotic agents with similar function, can provide and sustain the injured cells with the necessary energy source of ATP and anti-oxidants (such as ascorbic acid) which will aid to protect the tissues against progressing from reversible to irreversible injury.

When cyclocreatine or cyclocreatine phosphate is selected as the anti-apoptotic agent, as in some preferred embodiments of the invention, these compounds will be stored in tissues substantially in the form of cyclocreatine phosphate. During insult, the stored cyclocreatine phosphate can provide ATP to cells and protect the tissue from becoming injured. Creatine is phosphorylated chemically or enzymatically by creatine kinase to generate creatine phosphate, which is well-known (The Merck Index, No. 7315). Both creatine and creatine phosphate (also known as phosphocreatine) can be extracted from animal tissue or synthesized chemically. Cyclocreatine is an essentially planar cyclic analogue of creatine. Cyclocreatine is phosphorylated efficiently by creatine kinase in the forward reaction both in vitro and in vivo (Rowley, 1971).

Within the context of the methods of the invention and the compounds and compositions, the compounds and compositions may be pharmaceuticals. As such, any pharmaceutically acceptable salt of an anti-inflammatory agent or an anti-apoptotic agent can be administered, and can be considered within the term "compound" or "composition". By "pharmaceutically acceptable salt", it is meant art-recognized pharmaceutically acceptable salts. Typically these salts are capable of being hydrolyzed under physiological conditions. Examples of such salts include sodium, potassium, and hemisulfate. The term further is intended to include lower hydrocarbon groups capable of being hydrolyzed under physiological conditions, such as groups that esterify the carboxyl moiety, e.g., methyl, ethyl and propyl. For example, salts of cyclocreatine can be administered, rather than cyclocreatine.

Additionally, the agents of the invention can be administered either in substantially pure form, or as part of a composition including a pharmaceutically acceptable carrier, as is well-known in the art. "Pharmaceutically acceptable carrier" is intended to include substances capable of being co-administered with the anti-inflammatory agent or an anti-apoptotic agent and that allows the active agent to perform its intended function. Examples of such carriers include solvents, dispersion media, adjuvants, delay agents, and the like.

The administration of compositions of the invention preferably is carried out by oral administration as a powder, or by injection, although any means of administration may be used. Injection is usually employed within a fluid carrier, such as a sterile saline solution, with intravenous injection being preferred when the treatment involves post-ischemic events. Such pharmaceutically acceptable carrier solutions typically have an essentially neutral pH, such as the conventionally employed saline solution. Means for injection include, but are not limited to, intravenous, intraperitenially, intramuscular, and intradermally. In some cases, administration may be initiated prior to tissue injury and continued during and following injury.

Of course, other appropriate means of administration can be used depending upon the particular tissue of concern and the vehicle used for its administration. Administration may include inhalation, with or without other means for administering compositions of the invention. Compositions can also be given topically (e.g., eye drops, lotion, cream, etc.) or transdermally.

The invention also provides for use of an anti-apoptotic agent, such as cyclocreatine, cyclocreatine phosphate, coenzyme Q10, L-carnitine, glutathione, or α-lipoic acid, alone or in combination with a tissue-derived anti-inflammatory agent or agents to (a) treat (protective and therapeutic) injured tissues with the goal of protecting "normal" cells from becoming reversibly or irreversibly damaged, (b) revert the reversibly injured tissues back to normal, and (c) prevent the progression of the reversibly injured tissues toward irreversible damage.

Among the many methods and results provided by the invention, it is to be noted that the invention can provide a treatment for diabetic retinopathy that eliminates the destruction of photoreceptors by high-energy laser light and its resultant scarring.

In some embodiments, the method provides a treatment regimen associated with a screening test that can be employed not only pre-symptomatically following detection, but also as an immediate treatment and continuing maintenance program. Included in this embodiment is the provision for the use of antagonists, blockers, and other inhibitors, including endogenous inhibitors of tissue-specific leukocyte chemotactic factors. These antagonists can be employed as anti-inflammatory and neutrophic agents to protect cerebral, ocular and neural tissue from ischemic and inflammatory injury. Included as well is the provision for combinations of tissue-protective antagonists that impart to the tissue a tissue-specific anti-inflammatory response that delays depletion of ATP, conserves the adenylate pool in the tissue, buffers ischemic decrease in the ratio of ATP to ADP, delays exhaustion of high-energy phosphates, maintains cell membrane integrity, reduces intercellular edema, reduces the level of cell injury marker malondialdehyde, inhibits caspase enzyme activity, and/or reduces apoptosis. (Malondialdehyde is the end-product of lipid peroxidation by reactive oxygen species, a measurable endpoint.) These compositions further protect the brain, spinal column, and the retinal and optic nerve tissues against ischemic injury, inflammation, and pain while reducing intracellular edema and cell injury.

Yet another feature of the invention in embodiments is a method that provides the foregoing at an early stage in the pathogenesis of age-related macular degeneration and thereby stabilizes the disease and possibly reverses hypoxia induced oxidative stress, injury to retinal pigment epithelium and choroicapillaries and the formation of an abnormal extracellular matrix.

In another embodiment, the invention provides a treatment effective for retinal diseases secondary to ischemia, inflammation, and pain. The present invention provides for early detection, monitoring, and treatment of patients with diabetic retinopathy and age-related macular degeneration, including early retinal damage and vascular leakage, as well as neovascularization due to chronic and low-grade sub-clinical inflammation. In one embodiment, the retinal-derived leukocyte chemotactic factor released by ischemic and inflamed retina can be used to develop a blood test for early diagnosis, and monitoring of diabetic retinopathy and macular degeneration and related diseases. Antagonists to the retinal factor can be provided as anti-inflammatory agents and used to control the damaging effect induced by inflammation. These retinal factor antagonists can be used in combination with anti-apoptotic agents, such as creatine analogues and mitochondrial metabolites, to maintain elevated levels of energy nucleotides and anti-oxidants during ischemia and perfusion. This treatment can reduce the chronic sub-clinical inflammation that occurs early in diabetic retinopathy and macular degeneration, inflammation that can result in retinal damage and retinal vascular leakage/neovascularization and ultimately blindness.

In accordance with the present invention, the tissue-derived anti-inflammatory agents will have the advantage of reducing inflammation-mediated tissue damage and restoring tissue function without affecting the host immune system in the manner observed, for example, in cortisone treatment.

The present invention also provides a method that includes adding endogenous inhibitors to the tissue-derived anti-inflammatory agent(s) employed to control damage induced by inflammation. That is, it provides methods and compositions utilizing compositions having multiple bioactive agents. An anti-inflammatory cocktail could further comprise tissue factor inhibitors, endogenous inhibitors of the factor, anti-oxidants, and enzyme inhibitors that can be used in various combinations to specifically eliminate inflammation-mediated tissue damage during reperfusion and restore function without affecting the healing process that follows.

The present invention thus provides a method of achieving prompt recovery of functionality in animal, and in particular mammal, tissue. The method comprises the step of administering, preferably by injection, infusion, or orally, an effective amount of an anti-apoptotic agent prior to the onset of ischemia, or after tissue infarction, for preserving and fully restoring tissue functionality post-ischemia. The method can treat maladies with anti-inflammatory agents. The malady can be a metabolic injury, as well as ischemia and infection, such as with as injurious agents. In embodiments, the treatment reduces inflammatory response in Avian influenza flu and Septic Shock Syndromes.

As a general matter, tissue-derived leukocyte chemotactic factors rapidly released in response to tissue injury and infection have the following characteristics:
  LCF is an early factor which appears on the top of the inflammatory cascade before the release of other inflammatory mediators. LCFs are typically released by injured tissues within just several minutes;
  LCF serves as the initial signal in the cascade of the events that leads to inflammation and pain. LCF not only recruits phagocytes to sites of injury, but also activates phagocytes and endothelial cells to release a number of pro-inflammatory cytokines and chemokines (e.g., LECAM, ICAM-1, ELAM-1, IL-1B, IL-8, and TNF-α), oxidants, and proteolytic enzymes such as N-acetyl-B-glucosaminidase, and collagenase type IV;
  LCF is not only an earlier factor, but also stimulates the release of a number of inflammatory mediators which play a key role in the initiation and progression of the atherosclerotic lesion (IL-1, TNF-α, IL-6, MCP-1, IL-18, ICAM, VCAM, and Selectins), as well as in plaque destabilization and rupture (MMPs, MPO, IL-18, CD40L).

Specifically, Vascular Nourin is a marker of patients with various degrees of atherosclerosis (i.e., patients with Coronary Artery Diseases (CAD) also referred to as Stable Angina). Currently, the enzyme myeloperoxidase (MPO, EC 1.11.1.7) is used as a marker of plaque destabilization/rupture before patients have formed clots and experienced myocardial ischemia (acute coronary syndromes) in the form of unstable angina or heart attack. Nourin is present much earlier than MPO and like N-acetyl-B-glucosaminidase, Nourin will stimulate the release of MPO from neutrophils. Unlike MPO, which is a non-specific enzyme released by activated neutrophils, Nourin is tissue-specific. Furthermore, unlike MPO levels, which are influenced by the presence of anti-inflammatory drugs such as steroids, NSAIDS, and Statins, Nourin as a blood marker is not influenced by these anti-inflammatory drugs (steriods, NSAIDS, Statins).

One particular example of an LCF is the sequence MIINHNLAAINSH (SEQ ID NO:1). In FIG. 1, "Nourin" refers to a class of polypeptides comprising SEQ ID NO:1 as well as all "Nourin-1" sequences disclosed in U.S. patent application publication number 2006/0063198, which is herein incorporated by reference in its entirety.

In the tissue-derived leukocyte chemotactic factor family, it is thought (but without being limited to any particular theory) that the active peptide has a molecular weight of about 3 KDa and is associated with a large molecular weight carrier of 30-300 KDa. The association of the 3 KDa peptide with the large carrier is an ionic, non-covalent bond. In one example, a tissue LCF appears as a monomer in the 3 KDa band in a reduced SDS-PAGE gel. However, in a non-reduced SDS-PAGE gel, this tissue LCF appears as both a monomer in the 3 KDa band and a dimer in the 6 KDa band. MALDI analysis indicates that the 3 KDa and 6 KDa SDS-PAGE gel bands share similar peptide masses.

The LCF is stable over prolonged times when it is kept frozen (such as at a temperature of −20° C.), and as a lypholized powder kept at room temperature. The LCF is stable when kept in a refrigerator for 7 days. In addition, the release of the LCF is not inhibited in animal models pre-treated with dexamethasone or NSAIDS, suggesting that the pathway(s) for the formation of the LCF is independent of the arachidonic acid pathway. The release of the factor is associated with the induction of acute and chronic inflammation. The injection of the LCF induces acute and chronic inflammatory characterized by extensive leukocyte infiltration, as well as fibrin and collagen deposition.

The members of the LCF family, however, differ in their isoelectric points, solubility in organic solvents, heat stability, and mode of release. For example, the cardiac LCF has a pI of pH=7-8, while the gastric factor has a pI of pH=5.6-6.5 and the corneal derived factor has a pI of pH=8.5. Furthermore, the gastric factor is extracted into organic solvents and is heat-stable, while the cardiac and corneal factors are not extracted in organic solvents and are heat-sensitive.

Tissue-derived LCFs are a class of inflammatory mediators for leukocytes and endothelial cells. The LCFs not only stimulate endothelial cells and leukocyte chemotaxis, adhesion, and activation, but also stimulate the release of a number of pro-inflammatory cytokines and chemokines including but not limited to Interleukin-1 (IL-1), Interleukin-8 (IL-8), and tumor necrosis factor-alpha (TNF-α) by leukocytes and endothelial cells.

The present invention relates, in some aspects, to control of damage induced by inflammation and apoptosis induced by hypoxia/ischemia, infections, and/or inflammatory mediators such as TNF-α. For infection, this invention can protect tissues against hypoxia and the prolonged immune system overload, which kills people when infected with infectious agents such as anthrax, Avian bird flu, and endotoxin-induced septic shock. Treatments can include any number of combinations of therapeutic compositions comprising one or more anti-inflammatory agents effective to inhibit the release of tissue-derived LCFs, and in some embodiments, further comprising one or more anti-apoptotic agents.

The number of molecules capable of eliciting chemotactic responses is relatively high, and we can distinguish primary and secondary chemotactic molecules. Formyl peptides are di-, tri-, and tetrapeptides released in vivo from cells. A typical member of this group is the N-formyl-methyonyl-leucyl-phenylalanine (fMLF) (SEQ ID NO:11).

N-Formylmethionine (fMet) is an amino acid found in all living cells. It is a derivative of the amino acid methionine. It is a modified form of methionine in which a formyl group has been added to a methionine's amino group. fMet is a starting residue in the synthesis of proteins in prokaryotes and, consequently, is always located at the N-terminal of the growing polypeptide. fMet is delivered to the ribosome (30S) mRNA complex by a specialized tRNA, tRNA.fMet, which has a 5'-CAU-3' anticodon that is capable of binding with the AUG start codon located on the mRNA.

N-Formylmethionine is coded by the same codon as methionine, AUG. However, AUG is also the translation initiation codon. When the codon is used for initiation, N-formylmethionine is used instead of methionine, thereby forming the first amino acid of the nascent peptide chain. When the same codon appears later in the mRNA, normal methionine is used. Many organisms use variations of this basic mechanism.

The addition of the formyl group to methionine is catalyzed by the enzyme transformylase. This modification is done after methionine has been loaded onto tRNA.fMet by aminoacyl-tRNA synthetase. Methionine can be loaded either onto tRNA.fMet or tRNA.Met. Transformylase will catalyze the addition of the formyl group to methionine only if methionine has been loaded onto tRNA.fMet and not onto tRNA.Met, in which case the methionine will not be formylated.

Formylmethionine and non-formylmethionine ligands of the Formyl Peptide Receptors (FPR) are a class of ligands that are potent leukocyte chemotactic factors rapidly released by injured tissues (within about 5 minutes). The FPR competitive antagonist t-Boc-Phe-Leu-Phe-Leu-Phe (SEQ ID NO:2) significantly inhibits the function of LCFs on leukocyte chemotaxis. Similarly, although the immunosuppressor drug Cyclosporin H (CsH) inhibits leukocyte activation induced by the FPR ligand fMLF (SEQ ID NO:11), CsH does not inhibit leukocyte activation (release of histamine by basophils) induced by C5a, IL-8, platelet activating factor, monocyte chemotactic activating factor, RANTES, bryostatin 1, or phorbol myristate, indicating that these stimulants do not appear to function through the FPR (de Paulis, 1996).

"RANTES" (Regulated upon Activation, Normal T-cell Expressed, and Secreted) is an 8 KDa protein classified as a chemotactic cytokine or chemokine. RANTES is chemotactic for T cells, eosinophils, and basophils and plays an active role in recruiting leukocytes into inflammatory sites.

Chemokines belong to a special class of cytokines. Their groups (C, CC, CXC, CX3C chemokines) represent not only structurally related molecules with a special arrangement of disulfide bridges, but their target cell specificity is also diverse: CC chemokines act on monocytes (e.g., RANTES), and CXC chemokines are neutrophil granulocyte specific (e.g., IL-8).

FPR antagonists which inhibit neutrophil chemotaxis include, but are not limited to:
Spinorphin (Leu-Val-Val-Tyr-Pro-Trp-Thr, SEQ ID NO:3);
Tynorphin (Val-Val-Tyr-Pro-Trp, SEQ ID NO:4);
The synthetic pentapeptide t-Boc-Phe-D-Leu-Phe-D-Leu-Phe, SEQ ID NO:2;
The synthetic peptide t-Boc-Methionyl-Leucyl-Phenylalanine (t-Boc-MLF), SEQ ID NO:5;
Substance P antagonist R(dextro-)PKP(dextro-)FQ(dextro-)WF(dextro-)WLL-NH$_2$), SEQ ID NO:6;
Bile acids;
Cyclosporine H;
Pentoxifylline;
Antibodies against FPR;
Soluble FPR receptor (17 amino acid loop; RKAMGGH-WPFGWFLCKF; SEQ ID NO:12);
Spinorphin is an endogenous 7 amino acid peptide of Leu-Val-Val-Tyr-Pro-Trp-Thr (SEQ ID NO:3), which can be isolated from bovine spinal cord and inhibits both inflammation and pain. In vitro, spinorphin inhibits neutrophil chemotaxis induced by the formylmethionine peptide FMLF (SEQ ID NO:11), and is an important endogenous regulator for inflammation. Spinorphin may exert its endogenous anti-inflammatory activity by competing with the leukocyte chemotactic factors on the FPR sites and blocking leukocyte function. Spinorphin can regulate not only inflammation but also pain. The proprotein of spinorphin is not known. However, spinorphin has a structure resembling that of the hemoglobulin B-subunit which exhibits opioid activity. Spinorphin and tynorphin (Val-Val-Tyr-Pro-Trp, SEQ ID NO:4) which can be isolated from monkey brain tissue likely attenuate nociception via the inhibition of enkephalin-degrading enzyme.

Enkephalins are possibly involved in pain-modulating mechanisms in the spinal cord and are short-lived because of rapid degradation by various endogenous enzymes. Kyotorphin is a brain-derived protein which produces an analgesic effect by increasing the release of Met-enkephalin. The endogenous spinorphin also increases the levels of enkephalin and relief pain by inhibiting enkephalin-degrading enzymes. Neuropeptides such as Substance P (Met-at C terminal), and bradykinin (H-Arg-Pro-Pro-Gly-Phe-Ser-Pro-Phe-Arg-OH, SEQ ID NO:7 or K-Arg-Pro-Pro-Gly-Phe-Ser-Pro-Phe-Arg-OH, SEQ ID NO:8) induce some inflammatory responses.

Substance P is a neuropeptide with inflammatory properties. It is one of the tachykinins, such as bradykinin, which have contractile effects. The protein sequence of Substance P is RPKPQQFFGLM-$NH_2$ (SEQ ID NO:9). This sequence has been shown to stimulate neutrophil chemotaxis presumably at the Formyl Peptide Receptor (FPR). In this case, the terminal Met is at the end of the C-terminal. The Substance P antagonist R(dextro-) PKP(dextro-)FQ(dextro-)WF(dextro-)WLL-$NH_2$ (SEQ ID NO:6) inhibits neutrophil-induced chemotaxis by Substance P. It is likely that this Substance P antagonist also inhibits LCF function. Furthermore, the migratory effect of Substance P on neutrophil chemotaxis is expected to be inhibited by spinorphin, which also inhibited LCF action on neutrophil chemotaxis.

Blockers of formyl peptide receptors also include soluble receptors. Clinically, soluble fragments of the receptors of the inflammatory mediators TNF-α and Interleukin-1 are used in patients with rheumatoid arthritis to inhibit the progress of disease and tissue destruction. Similarly, soluble portions of formyl peptide receptors can also be effective in inhibiting leukocyte migration induced by endogenous formyl peptides. Furthermore, the synthetic compound t-Boc-Phe-Leu-Phe-Leu-Phe (SEQ ID NO:2) as well as the truncated 17 amino-acid loop composed of the tail region of the FPR and having hydrophobic character, can both be effective in inhibiting leukocyte migration induced by endogenous formyl peptides.

Cyclosporine H (CsH) is an immunosuppressive drug which also acts on leukocyte FPR to inhibit their function. Addition of other anti-inflammatory agents known in the art, such as nimbidin, can be done to help control inflammatory diseases secondary to chemotherapy treatment and chemical toxicity, for example. Nimbidin is a mixture of tetranortriterpenes and is known to possess potent anti-inflammatory and anti-arthritic activities.

Monoclonal antibodies against LCFs can also significantly inhibit neutrophil chemotaxis and the release of, for example, IL-8 by neutrophils.

Cytokine-storm antagonists include: spinorphin, spinorphin plus leuhistin, tynorphin; t-Boc-Phe-Leu-Phe-Leu-Phe (SEQ ID NO:2), the synthetic peptide t-Boc-Methionyl-Leucyl-Phenylalanine (t-Boc-MLP, SEQ ID NO:5), the immunosuppressive cyclosporine H, the FPR antagonist Carbobenzoxy-phe-met (SEQ ID NO:10), the entire FPR, or at least one soluble receptor, the truncated 17 amino acid loop of the FPR, pentoxifylline, trasylol protease inhibitor, anti-oxidants, antibiotics, monoclonal antibodies against LCFs, monoclonal antibody against FPR which inhibits cell activation, cyclocreatine analogues, and salts thereof.

The methods of the present invention can further include, in some embodiments, delivery of exogenous nitric oxide (NO). Because it can be difficult to administer NO directly, it is preferred to administer to the mammal an agent that is capable of generating nitric oxide in vivo. Delivery of exogenous NO, either administered directly or through release by an agent that is capable of generating nitric oxide under physiological conditions, can be a good therapeutic option in the treatment of diseases resulting from ischemic episodes, and improve the effectiveness of compositions of the invention. Specifically, NO can alleviate vascular spasm due to reduction of NO which occurs after ischemia. Furthermore, there may be a synergy between the vascular relaxation effects of NO and the greater availability of ATP from an agent, since NO is required for the formation of cGMP, the cofactor essential for the kinase. This is the biochemical basis for the beneficial effects of compounds such as nitroglycerin, an NO producer, in relieving angina attacks. Many NO providing compounds are known in the art, and include, among others, arginine and derivatives of it, which are broken down to release NO.

The present invention can be effectively administered at a plurality of times associated with tissue injury, including prior to actual injury, during various stages of injury, and after injury. Specifically, compositions and methods of the invention can be used prophylactically to protect a mammal against the development of tissue injury, such as in disease or infection. Compositions and methods of the invention can be used after the development of tissue injury for a short period of time, such as minutes to hours. Compositions and methods of the invention can also be used after the development of tissue injury for an extended period of time, such as days to weeks, months, or even years. Finally, compositions and methods of the invention can be used after the tissue injury has been alleviated (or there is reason to believe it has been improved), in an attempt to prevent the onset of a similar tissue injury in the future. It is intended that the terms "treat" and "treatment" encompass at least all of the variations described in this paragraph, as well as similar embodiments as will be appreciated by a skilled artisan.

The compositions and methods of the invention can be universally applied to virtually any mammalian tissue injury due to a variety of disease states, infections, or other reasons. Also, the mammalian tissue can be treated even if not actually present in a mammal when treated, such as during an organ-transplant procedure. Illustrative organ transplants include lung, kidney, skin, liver, cornea, bones, and nerve cells.

The methods of compositions recited herein can be effective for both acute and chronic inflammation. Examples of acute inflammation include stroke, peripheral arterial disease (PAD), optic nerve ischemia, pain, obesity, and stress. Examples of chronic inflammation include diabetic retinopathy and macular degeneration, diabetes, atherosclerosis, and rheumatoid arthritis. The methods of compositions recited herein can also be effective for infections, such as septic shock and anthrax; and/or tissue states associated with lethal cytokine storms such as Avian Influenza.

The compounds, compositions, and methods of the present invention have applicability in treatment of many tissue injuries and biochemical states within tissues and cells. Some non-limiting examples include: atherosclerosis, rheumatoid arthritis, brain ischemia and trauma, spinal cord ischemia and trauma, aortic cross clamping leading to spinal cord ischemia, kidney ischemia and trauma, liver ischemia and trauma, lung ischemia and trauma, muscle ischemia (e.g., PAD), inflammation, trauma, and atrophy, skin ischemia and trauma, ocular ischemia, degeneration, and inflammation, nervous system ischemia, degeneration, and inflammation, digestive system (e.g., esophagus, stomach, intestine, colon) ischemia, degeneration, and inflammation, spleen and pancreas ischemia, degeneration, and inflammation, ear, mouth, and nose ischemia, degeneration, and inflammation, bone marrow ischemia, degeneration, and inflammation, sexual organs ischemia, degeneration, and inflammation, dental tissues ischemia, degeneration, and inflammation.

Therapeutic applications of inhibitors of vascular LCF, to prevent and treat atherosclerosis, include, but are not limited to, the following: reducing the lesion size, reducing the formation of new plaques, reducing the size of plaques that already exist, stabilizing plaques and make them less prone to rupturing and forming clots, altering cellular composition of atherosclerotic lesions, inhibiting recruitment of phagocytes to vessels and accordingly inhibiting the foam cell formation of macrophages, limiting the progression of the atherosclerotic lesions, and reducing the progression of the atherosclerotic lesion.

Diabetes results in vascular damage and reduction of sufficient blood flow to tissues, leading to the development of a number of ischemia-related diseases such as diabetic retinopathy, peripheral artery disease, optic nerve ischemia, and cerebrovascular diseases. Injury to the vasculature also results in ischemia of nerve tissue and the development of many neurological diseases. Hydrogen peroxide as sometimes released as an injurious agent to tissues leading to the release of LCFs from tissues such as corneal endothelium and epithelium, retina, and the heart. The present invention can protect the vasculatures from damage secondary to diabetes, as well as other diseases that can also induce vascular injury such as in the case of anthrax infection, chemotherapy in cancer patients, patients experiencing various burns, etc. Ischemia and inflammation play a key role not only in stroke (brain ischemia) but also in the early pathogenesis of diabetic retinopathy and age-related macular degeneration. Diabetic retinopathy is a leading cause of blindness worldwide.

With regard to cerebral and peripheral nerve tissue, it is understood that stroke is one of the leading causes of death and long-term disability in the United States. There are two forms of stroke: ischemic, characterized by blockage of a blood vessel supplying the brain and the resultant cessation or reduction of blood flow; and hemorrhagic, characterized by bleeding into or around the brain. The present invention can treat stroke of the ischemic and hemorrhagic type.

It is known that the arterial wall is one of the most poorly oxygenated tissues in the mammalian body. In larger arteries, the central part of the arterial wall is very poorly supplied with oxygen and other nutrients. Using an atherosclerotic rabbit model, it was reported that hypoxia, low ATP content, high lactate content, and low glucose content were shown in the atherosclerotic lesions as well as in the media (Bjornheden et al., 1999). These studies suggest that hypoxia and energy deficiency may be major contributors to the generation of central necrosis in atherosclerotic lesions. Hypoxia may stimulate the release of vascular LCF and contribute to the inflammatory response in the plaque. Vascular LCF may also stimulate the release of a number of inflammatory mediators which are involved in the development of atherosclerotic lesions, including cytokines such as TNF-α, IL-1, IL-6, and IL-8; adhesion molecules such as Selectins, MPO, and MCP-1, which recruit monocytes and lymphocytes and promotes plaque destabilization. Vascular LCF can play a crucial role in the initiation and propagation of atherosclerosis.

A number of studies support an important role of diet and inflammation in the risk of a variety of chronic diseases, including diabetes, atherosclerosis, vascular diseases such as peripheral artery disease, and cerebrovascular diseases and overall mortality (see, for example, Esposito K, Diet and inflammation: a link to metabolic and cardiovascular diseases, Euro Heart J, 27(1):15-20, 2005). Evidence is available indicating that the generation of a pro-inflammatory milieu might be one mechanism through which unhealthy diets are linked to metabolic and vascular diseases. Understanding the link between diet and inflammation holds the premise to elucidate the mechanisms by which dietary patterns improve cardiovascular health.

More evidence is building in support of the idea that obesity causes inflammation and that chronic inflammation is a major cause of many degenerative diseases and accelerates aging. Published studies reported that circulating monocytes and lymphocytes exist in a pro-inflammatory state in obese persons known to be at increased risk of developing diabetes, vascular disease, stroke, etc. Pro-inflammatory factors were significantly higher in blood samples from obese subjects than the average weight and that the index of insulin resistance in the obese subjects was nearly three times higher than that of the normal subjects. The hyper inflammatory status interferes with insulin signaling which results in insulin resistance and ultimately diabetes. In diabetic patients, there is an increased circulating levels of cytokines such as TNF-α, Interleukin-6, Interleukin-18, and C-reactive protein (CRP—a marker of endothelial dysfunction) (Ceriello A, Evidence for an independent and cumulative effect of postprandial hypertriglyceridaemia and hyperglycaemia on endothelial dysfunction and oxidative stress generation. Circulation, 2002, 106:1211-1218). Changing diets and losing body weight, however, was shown to significantly reduce the levels of cytokines and insulin resistance.

Macronutrient intake may produce oxidative stress and inflammatory responses. The raised flux of nutrients in the post-prandial state is associated with an increase in circulating levels of pro-inflammatory cytokines, recruitment of neutrophils, and oxidative stress. Diet reach in natural anti-oxidants (fruits, vegetables), the elimination of trans-and saturated fatty acids intake, and increasing the consumption of omega-3 fatty acids were shown to be associated with reduced inflammatory status (Esposito K, Diet and inflammation: a link to metabolic and cardiovascular diseases, Euro Heart J, 27(1):15-20, 2005). Interestingly, emotional states have a large influence on body inflammation. People who are prone to anger, hostility, and depressive symptoms respond to stress with increased production of the stress hormone norepinorphine. The increase in this stress hormone activates the inflammatory arm of the immune system resulting in chronic, low-grade inflammation. Therefore, it was recommended that losing excess weight and lower daily stress will lower the level of body-wide inflammation and the person will live longer.

We have shown that Nourin is a key early inflammatory mediator released by various tissues in response to oxidative injury, nutritional factors including vitamin A deficiency, and infections (viral and bacterial). In case of obese individuals, Nourin is similarly released in response to injury induced by oxidized cholesterol namely oxidized LDL. Nourin also activates leukocytes and vascular endothelial cells to release a number of chemokines and cytokines including adhesion molecules, IL-1, IL-8, IL-6, and TNF-α. As early initial signal in the inflammatory cascade, Nourin can be used both as a "disease marker" and "therapeutic target".

Adipose tissues acquire an influx of new blood vessels to support the increased nutritional demands. Adipocytes release angiogenic factors to induce this process. This means that the variety of pro-and competent inflammatory cytokines that have been stimulated by the early marker nourin can have ready access to the adipose tissue and exert their deleterious effects on the host. If nourin significantly mobilizes VEGF for example, this would be an additional reason to devise inhibitors for nourin.

MCP-1 is involved in the initiation of the fatty streak by recruiting monocytes and lymphocytes, promotes plaque destabilization. MCP-1 is a member of the chemokines (C—C) family with molecular weight of 10 KDa (102 aa). It is not induced, however, by ischemia as Nourin does and it is induced only after postischemia during reperfusion and, accordingly, it is considered as a late chemoattractant after C5a. Treatment of human endothelial cells with oxidized LDL also induced MCP-1 secretion. Nourin will be released earlier than MCP-1 in response to both hypoxic injury and oxidized LDL treatment.

Diagnostically, the blood levels of Nourin alone and in combination with other inflammatory mediators such as IL-1, IL-8, IL-6, TNF-α, and CRP could serve as an easy "early warning" for inflammation in obese and stressed individuals. Nourin is much earlier than CRP as a marker of endothelial dysfunction and disease development. Unlike CRP which is a non-specific inflammatory mediator released by liver in response to injury, Nourin is a tissue specific marker. Therapeutically, anti-inflammatory drugs such as Nourin antagonists and anti-apoptotic drugs such as cyclocreatine will be useful in controlling inflammation associated with obesity and stress and accordingly prevent the development of a number chronic diseases including diabetes, cardiovascular, and cerebrovascular disease.

In general, a cytokine storm is induced by viral infection (e.g., seasonal and Avian influenza flu), gram-negative bacterial infection (endotoxin), and also in patients infected with virus and then gram-negative bacterial infection due to a compromised immune system. The systemic expression of a healthy immune system results in the release of many pro-inflammatory mediators including chemokines, cytokines, oxygen free radicals, digestive enzymes, and coagulation factors and can lead to organ failure and death. Key pro-inflammatory cytokines are TNF-α, Interleukin-1 (IL-1), InterLeukin-8 (IL-8), and Interleukin-6 (IL-6), as well as anti-inflammatory cytokines such as Interleukin-10 and Interleukin-1 receptor antagonist.

The tissue-derived Nourin released shortly after Avian viral infection or the lethal bacterial infection such as *E. coli* will be one of the key inflammatory mediators that activate resident macrophages and recruit leukocytes to release high levels of adhesion molecules, proteolytic enzymes, oxidants, chemokines and cytokines including IL-1, IL-8, IL-6, and TNF-α. The early release of Nourin by viral and bacterial infected tissues and its key role in evoking the observed cytokine storms will, therefore, be the basis for developing therapeutic products aimed at combating excessive host inflammatory response which kills patients infected with for example the Avian influenza and *E. coli*. Therapeutic products aimed at reducing the levels of the tissue-derived Nourin will also inhibit the levels of several pro-inflammatory mediators including TNF-α and, therefore, additionally protect tissues from TNF-α induced apoptosis.

LCFs stimulate local tissues and immune cells to release key chemokines and cytokines of the cytokine storms which result in organ failure and death. LCF antagonists can play a key role in controlling host inflammatory reactions caused by the Avian flu virus which forces the body's immune system into overdrive, attacking internal organs. In some embodiments, LCF antagonists are not affected by changes in viral strains or virus mutations and specifically inhibit the cytokine storms without being subjected to viral resistance (a significant concern for current viral medications). In preferred embodiments, the treatment comprising LCF antagonists is specific to inhibit LCF-induced cytokines without affecting the host defense immune system.

Anthrax is a lethal gram-positive bacterium that lacks endotoxin. Despite the long history of *B. anthracic* as a human and animal pathogen and its notoriety as an agent of biological warfare, exactly how anthrax kills the host is unclear (Prince, 2003). Major pathological observations include vasculitis (vascular inflammation of small and large vessels), vascular apoptosis, edema, endotoxin shock-like cytokine storms, hypoxia, apoptosis and necrosis of major organs, organ failure, hemorrhage, and death of the mammal. *Bacillus anthracis*, the causative agent for anthrax, produces three polypeptides that comprise anthrax toxin. These are protein antigen (PA), lethal factor (LF), and edema factor (EF). The lethal factor is a matrix metalloproteinase enzyme while the edema factor is an adenylate cyclase enzyme.

In a pathological study of human inhalational anthrax after a large outbreak in Sverdlovsk, Russia, hematogenous spread of *Bacillus anthracis* was found to be associated with capillary and vascular lesions that consist of fibrin deposition and various amount of neutrophic infiltrate surrounding the vessel wall (Grinberg, 2001). The capillaries and vasculitis weakened the vessel wall and produced high-and low-pressure hemorrhages (Grinberg, 2001). Injecting corneal LCF into rabbit anterior chamber resulted in neutrophil and fibrin accumulation, as well as corneal edema within two hours (Elgebaly, 1994). It has further been demonstrated in vitro that neutrophils induce endothelial damage and denude the membrane leading to edema (Elgebaly, 1984).

In some embodiments of the present invention, a composition comprising cyclocreatine can be effective to moderate the edema associated with anthrax. Anthrax edema toxin (ET) consists of a protective antigen (PA) and an adenylate cyclase edema factor (EF), which is a Ca++/Calmodulin enzyme. The massive production of cyclic AMP (cAMP) from *B. anthracis* infection is associated with prominent inflammation and swelling of tissues. An analogous effect is produced by choleratoxin, e.g., cAMP is a ubiquitous cofactor for many protein kinases, some of which are involved in rapid changes in capillary permeability. Such enzymes require ATP to function. The creatine kinase pathway has a critical role in the efficient mobilization and use of ATP for energy. The natural substrate, creatine (Cr), exchanges high energy phosphate (~P) with ADP in the kinase reaction. However, an unnatural substrate, cyclocreatine (CCr) can also participate in the kinase reaction. The transfer of ~P from CCrP to ADP is at a significantly lower rate than the comparable reaction with CrP.

Therefore, it is hypothesized (without being limited to any particular theory) that CCr may compete for available ATP with kinase enzymes dedicated to changes in vascular permeability which require cAMP for activity. In other words, the EF (adenylate cyclase) that produces cAMP would encounter a reduced pool of ATP in the presence of a given concentration of CCr. The latter has been shown to be relatively innocuous in mammalian systems. Significant roles for prostaglandins and histamines are known in the inflammatory cascade. With respect to ET it has recently been shown that the use of PGE synthase inhibitors (Celecoxib) and histamine antagonists (Cromolyn) has ameliorated the edematous effects of ET (Tessier et al., 2007). Because these events occur distal to the generation of cAMP, the administration of CCr together with requisite antibiotics should be considered in the treatment of anthrax infection, especially the inhalational kind.

It is known that L-histidine, at pharmacological levels (such as about 10 mM), can inhibit the matrix metalloproteinases (MMP) of the cytokine Autotaxin. The latter is a tumor cell-associated moiety that hydrolyzes a phospholipids substrate to yield a potent cytokine that has motogenic and mitogenic properties. The amino acid has also been shown to inhibit a gelatinase activity (Clair, 2005). L-histidine is quite specific and can be an effective agent in the compositions of the invention when applied to treat anthrax infection. In preferred embodiments, anthrax is treated with an anti-inflammatory agent comprising LCF to inhibit early events such as vasculitis and vascular damage, an anti-apoptotic agent to protect tissue from late events such as hypoxia and apoptosis (and resultant organ failure), and L-histidine to protect against the damaging effect of MMP.

The present invention can be used for mammalian patients who will undergo nerve-related surgery, such as aneurysms, tumor, intracerebral hemorrhage surgery, and other similar procedures (e.g., neuromuscular diseases), as well as patients who will undergo "non-nerve" related surgery that is capable of causing ischemia of the nervous system. The system includes the administration of effective agents (as described above) before, during, and after ischemia to preserve and restore nerve function before and during reperfusion.

The present invention can be used during many treatment stages mentioned above. It can be used prophylactically prior to ischemia to protect against stroke, ocular, and peripheral nerve damage in high-risk patients including aging populations, diabetic patients, patients with vascular diseases, and patients with prior transient ischemic attack (TIA). It can be employed prior to nerve-related and "non-nerve" surgery to protect against ischemic injury and neurologic complications. In addition, it can be used immediately after cerebral ischemic stroke to protect surrounding areas against tissue injury and loss of function, immediately after hemorrhagic stroke to protect surrounding areas against tissue injury and loss of function, immediately after ischemia of peripheral nerves to protect surrounding areas against tissue injury and loss of function, or immediately after head trauma to protect surrounding areas against ischemic and necrotic tissue injury and loss of function. It is also applicable immediately after spinal cord trauma or peripheral nerve trauma to protect surrounding areas against ischemic and necrotic tissue injury and loss of function. Finally, it can be employed as a maintenance treatment post-ischemia and post-reperfusion of nerve tissue to assure a healthy recovery and continued nerve tissue function.

Administration of an anti-apoptotic agent shortly prior to ischemia (for example, four days or less prior to an ischemic condition) can be effective to restore post-ischemic nerve function. Such administration can have application to high-risk patients to protect against ischemic damage and reperfusion, as well as to presurgical patients to prevent loss of nerve function associated with post-ischemic reperfusion.

Unlike tPA therapy, the treatments of the invention can be given to patients experiencing stroke attack as a result of hemorrhage or blockage to protect areas at risk and reduce disability. Additionally, it can be immediately administered to patients experiencing ischemic stroke upon presentation to an emergency room, even beyond the three-hour therapeutic time window that often leads to treatment disqualification with tPA. Unlike tPA therapy, the treatments of the present invention would not be expected to have neurotoxic or vasoactive side effects, alter the blood-brain barrier, or pose a risk of hemorrhage.

The effective amount of the at least one agent to be administered in the invention will depend on a number of factors associated with the type of injury, the patient, the properties of the agent or agents, and environmental conditions at the time of treatment. For purposes of illustration, effective amounts of preferred anti-apoptotic agents will be described. Sterile saline solutions containing substantially more than one percent and typically more than three percent by weight of cyclocreatine can be effective within three days of surgery, although somewhat lower percent levels of cyclocreatine may be effective when administered within five to seven days prior to surgery. The dosage administered may be as low as about 1 gram per 70 kilograms of body weight but typically is greater than about 5 g/70 kg. For cyclocreatine and cyclocreatine phosphate, a saturated solution of 0.1%-5% (or higher) of cyclocreatine and/or cyclocreatine phosphate can be prepared in saline or any other physiologic buffer.

Acetyl L-carnitine can be administered orally or as injection as low as 2 grams per 70 kilograms of body weight. Higher amount of acetyl L-carnitine can be used. Similarly, glutathione and ∀-lipoic acid can be administered each orally or as injection as low as 2 grams per 70 kilograms of body weight. Higher amount of $\alpha$-lipoic acid can be used.

EXAMPLES

The present invention will now be further characterized and understood by reference to the following non-limiting examples. The following paragraphs describe experimental procedures that demonstrate the beneficial effects of the administration of anti-inflammatory agents alone and in combination with anti-apoptotic agents in protecting tissues from injury induced by ischemia, inflammation, and pain. For these studies, animal models and cell culture models of tissue ischemia and inflammation that represent ischemia and infection were used.

Example 1

Release of Leukocyte Chemotactic Factors by Ischemic Spinal Cord Tissue

Three pigs were sacrificed and the spinal cord were immediately removed, cut, and incubated in Hank's Balance Salt Solution (HBSS) at room temperature (1 gm spinal cord/2 ml HBSS). After 5, 10, 20, 40, 60, and 240 minutes, 100 microliter (ul) aliquots of supernatant solutions were collected and tested for the level of neutrophil chemotactic activity using human peripheral neutrophils as indicator cells. Samples collected from the 2 hour incubation were also processed on the size exclusion HPLC using the 1-300 KDa column. Modified Boyden chambers were used to test for the chemotactic activity in aliquot samples as undiluted, as well as diluted 1:5, and 1:25 in HBSS. The synthetic f-Met-Leu-Phe (SEQ ID NO:11) ($10^{-9}$ Molar) was used as the positive control for 100% response, while HBSS was used as the negative control for random migration. Neutrophil migration was reported as chemotactic index of cell density (O.D. Units) using a LKB laser densitometer.

High levels of neutrophil chemotactic activity (75-95% of f-MLF (SEQ ID NO:11)) were detected as early as 5 minutes after ischemia. Activity continued to be detected (50-110% of f-MLF (SEQ ID NO:11)) for the additional four hour incubation. When culture supernatant solutions were fractionated using size exclusion HPLC (1-300 separation), high levels of chemotactic activity (50-100% f-MLF (SEQ ID NO:11)) was detected in fractions below 5 KDa. Activity was detected in undiluted, as well as fractions diluted 1:5 and 1:25. This finding demonstrates the release of a potent low-molecular-weight chemotactic factor from ischemic spinal cord tissue minutes after ischemia and that the release of the factor was sustained for the duration of ischemia.

Example 2

Alcohol-induced Inhibitors of Leukocyte Chemotactic Factors

Studies have shown the association between acute and chronic ethanol intoxication and lowered resistance to infection in these patients (Feliu, 1977). Impairment of neutrophil chemotaxis due to the presence of serum inhibitors was suggested as a major mechanism for the increased susceptibility to infection (VanEpps, 1975). To date, tissue(s) releasing these serum inhibitors has not yet been identified.

Because the mucosal side of the gastric tissue is the first to be exposed to ingested ethanol and is exposed to the highest concentrations for a length of time, we tested the capability of gastric mucosa exposed to ethanol to release inhibitors of neutrophil chemotaxis. The mucosal surfaces of rabbit stomachs were incubated for 60 minutes with 0.01% ethanol (VN) while the serosal sides were incubated with buffer. Results indicate that gastric tissue exposed to ethanol released inhibitors for neutrophil chemotaxis. Control non-ethanol treated gastric mucosal tissue released high levels of the gastric neutrophil chemotactic factor (Elgebaly, 1990). An average suppression of neutrophil chemotaxis compared to control non-ethanol treated gastric mucosal samples was 51%. There was no detectable level of ethanol in the serosal samples. When the serosal solutions of alcohol-treated stomachs were diluted 1:3 and 1:9 in PBS, the recovered chemotactic activity remained low in both dilutions indicating that the observed reduction in activity is not due to a desensitization effect on neutrophils but rather the presence of inhibitors.

Interestingly, when the serosal solutions of alcohol-treated mucosa were fractionated using an amicon Ultrafiltration membrane of molecular weight cut off 100 KDa, the high (above 100 KDa) and low (below 100 KDa) fraction inhibited neutrophil chemotaxis induced by C5a. The high and low molecular weight inhibitor reduced C5a-induced neutrophil chemotaxis by 54% and 53%, respectively. The nature of the high and low molecular weight tissue-derived LCF inhibitors could be endogenous competitive antagonists of C5a on neutrophil receptors, a proteolytic enzyme which non-specifically deactivates LCF and reduce their activity, or a "peptide deformylase" which deformylate N-formylmethionine peptides and reduce their activity (Nguyen, 2003).

The generation of these endogenous inhibitors of inflammation by local tissue indicates the capability of injured tissue to release both pro-and anti-inflammatory factors in response to various treatments. The generation of these gastric-derived immunosuppressor following alcohol consumption might increase the susceptibility of individuals to various infections including the Human Immunodeficiency Virus (HW). Results presented in this Example 2 support a role for alcohol as a cofactor in immunosuppressive disorders. Therefore, the present invention provides an opportunity to further identify, develop, and incorporate these endogenous inhibitors into the tissue specific anti-inflammatory cocktails employed to control damage induced by inflammation.

Example 3

Leukocyte Chemotactic Factors Released by Epithelial Cells Infected with H1N1 Virus We determined whether epithelial cells (Madin-Darby canine kidney cells-MDCK) grown in culture release LCFs in response to injury induced by laboratory-adapted influenza H1N1 virus. For these studies, MDCK cells were infected with the laboratory influenza virus H1N1 (PR8) for 1, 3, 6, 12, and 24 hours. Control cells were incubated with culture media only. At the various time points (1-24 hours), supernatant solutions were collected and tested for the presence and levels of chemotactic activity using standard modified chemotaxis chamber as a functional assay for chemotactic factors. Neutrophils isolated from human peripheral blood were used as the migratory cells.

Figure 2:
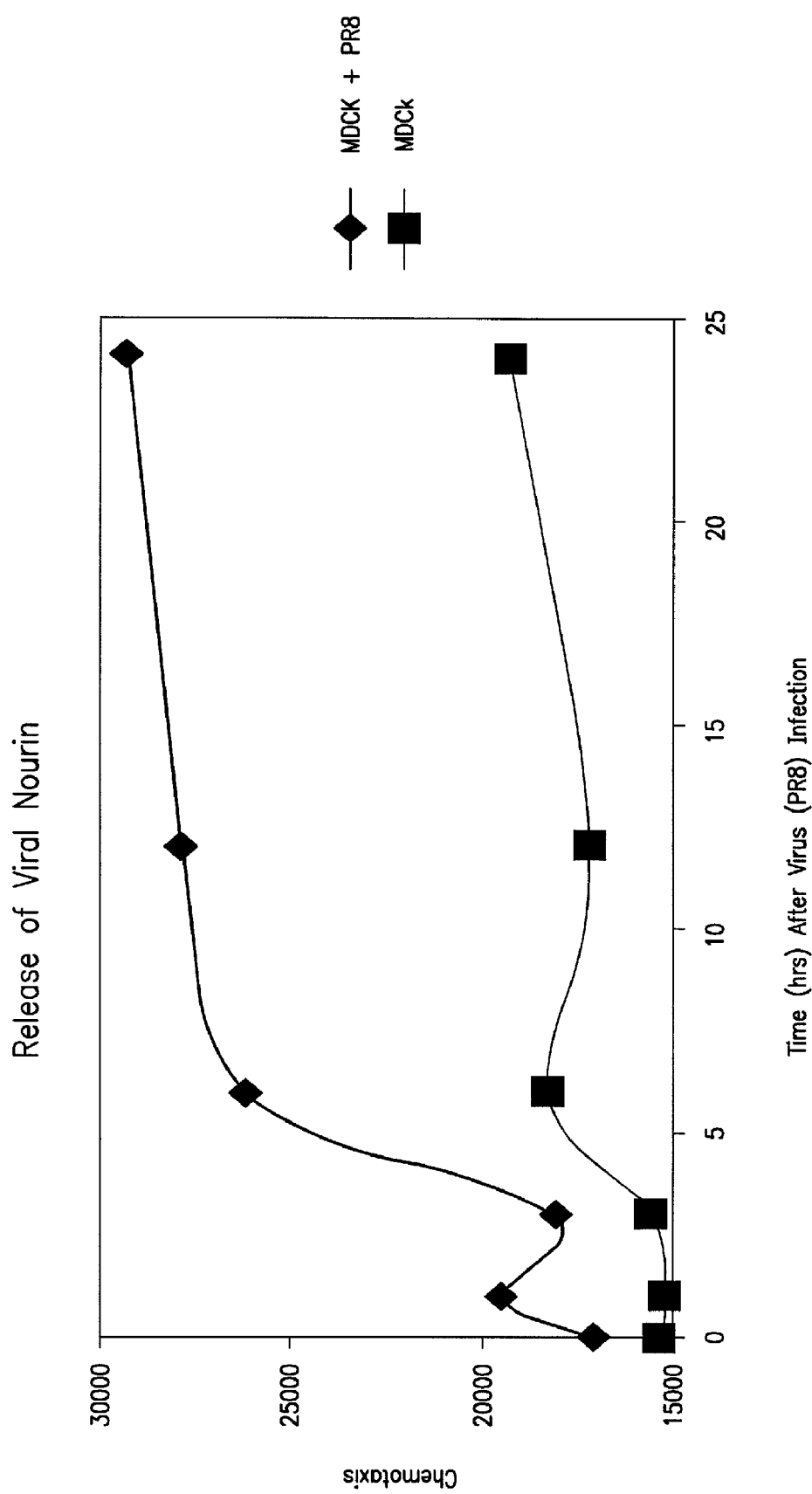
FIG. 2 is a plot showing the release of high levels of chemotactic activity from epithelial cells in response to viral infection with the laboratory-adapted influenza virus H1N1.

As described in FIG. 2, significant chemotactic activity is detected in supernatant solutions collected from H1N1 infected cells compared to control cells grown in culture without the virus. High levels of chemotactic activity were detected as early as 6 hours after viral infection and remained high for the remaining 24 hours of incubation. Control MDCK cells incubated with culture media released low levels of the chemotactic factors. This data suggests the ability of epithelial cells to quickly release (within first 6 hours) high levels of chemotactic factor (referred to as Nourin in FIG. 2) in response to influenza viral injury.

Figure 3:
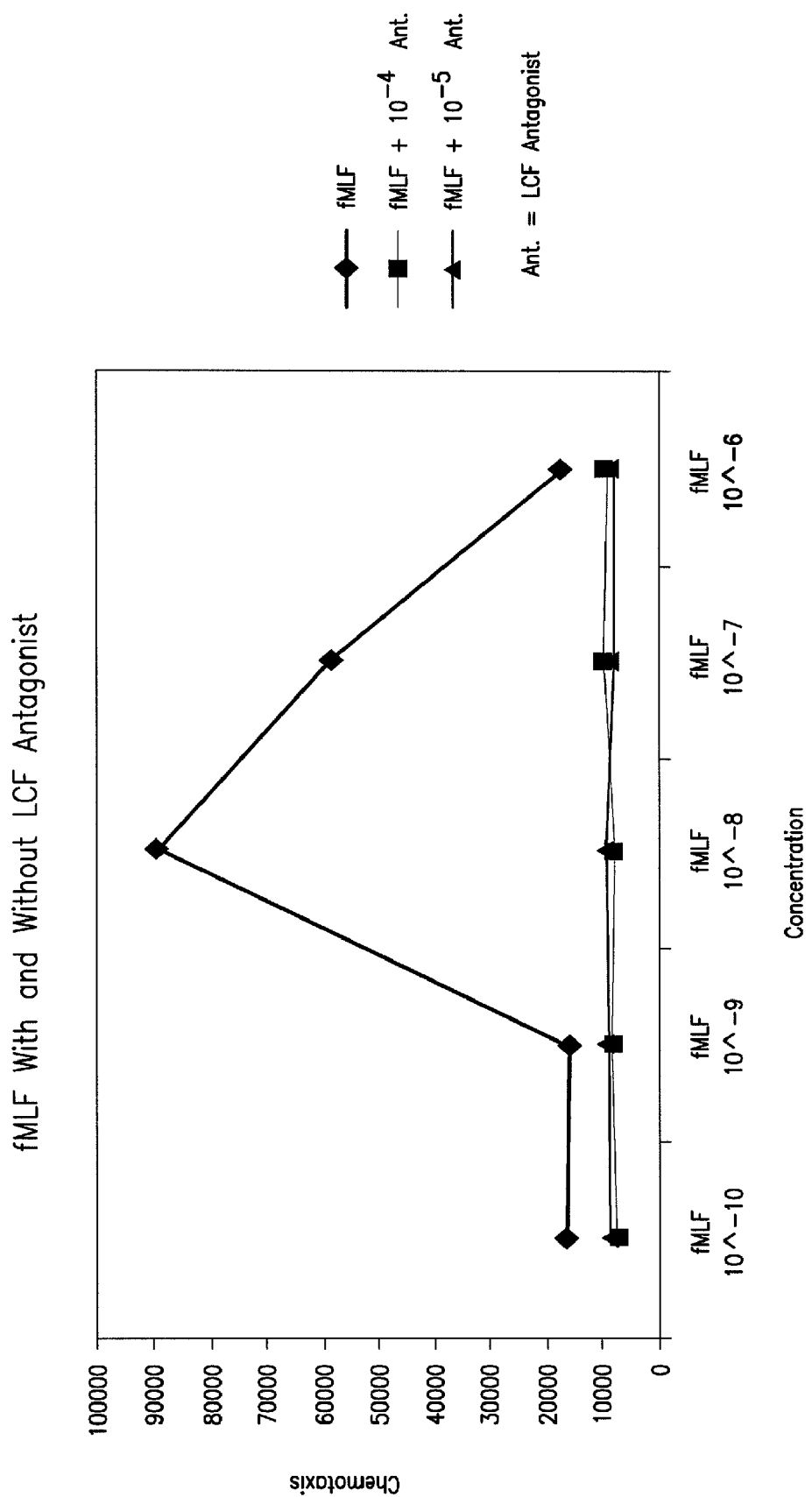
FIG. 3 is a plot demonstrating that a leukocyte chemotactic factor antagonist, t-Boc-Phe-Leu-Phe-Leu-Phe (SEQ ID NO:2), inhibits fMLF (SEQ ID NO:11) chemotactic activity (fMLF (SEQ ID NO:11) is the formylmethionine peptide f-Met-Leu-Phe (SEQ ID NO:11)).
Figure 4:
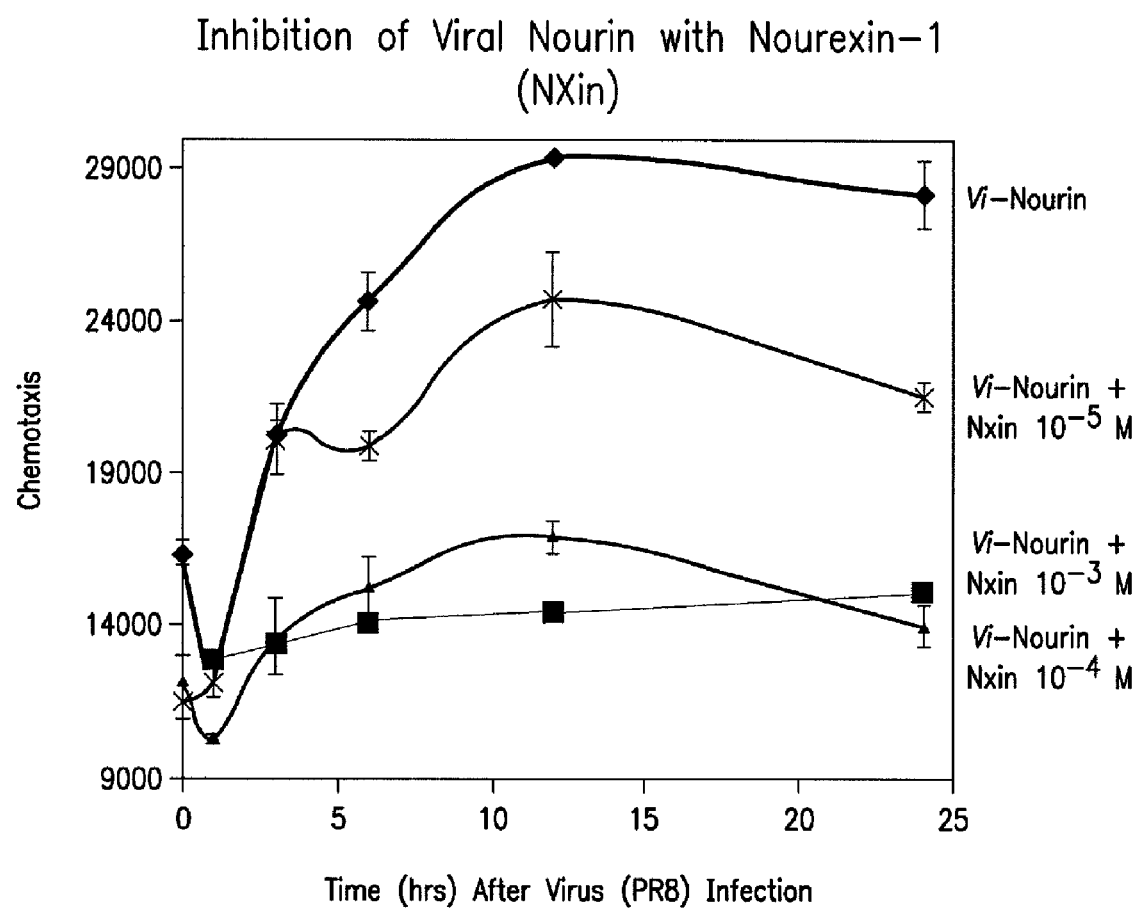
FIG. 4 is a plot showing that a leukocyte chemotactic factor antagonist, t-Boc-Phe-Leu-Phe-Leu-Phe (SEQ ID NO:2 and labeled as "Nourexin-1" or "NXin" in the figure) inhibits neutrophil chemotactic activity released by epithelial cells in response to viral infection with the laboratory-adapted influenza virus H1N1.

Results described in FIG. 3 and FIG. 4 indicate that an LCF antagonist of MIINHNLAAINSH (SEQ ID NO:1) significantly inhibited neutrophil chemotaxis induced by viral chemotactic factor (30%-100%) at concentrations ranging from about $10^{-5}$ to $10^{-3}$ Molar. The LCF antagonist is t-Boc-Phe-Leu-Phe-Leu-Phe (SEQ ID NO:2). These results suggest that at least one of the chemotactic factors released by epithelial cells in response to H1N1 viral infection is MIINHNLAAINSH (SEQ ID NO:1). Supernatant solutions used in this study were obtained from cultured MDCK cells incubated with the influenza virus H1N1 for 6 hours. FIG. 3 demonstrates that this leukocyte chemotactic factor antagonist inhibits fMLF (SEQ ID NO:11) chemotactic activity (fMLF (SEQ ID NO:11) is the formylmethionine peptide f-Met-Leu-Phe (SEQ ID NO:11)). FIG. 4 shows that this antagonist inhibits neutrophil chemotactic activity released by epithelial cells in response to viral infection with the seasonal influenza virus H1N1.

Example 4

Leukocyte Chemotactic Factors Released by Various Tissues in Response to Endotoxin Treatments We demonstrated the release of the 3 KDa LCF Nourin by a number of tissues in response to endotoxin treatments both in vitro and in vivo. In vitro, high levels of the 3 KDa Nourin was isolated from cultured human bladder fibroblasts treated with endotoxin for 6 hours. Culture supernatant solutions were collected and the low molecular weight Nourin (3 KDa) was isolated using size exclusion high performance liquid chromatography (HPLC). In vivo, rabbit eyes were injected intravitreally with 100 ng E. coli endotoxin. Control eyes were injected intramuscularly with 1 ml cod liver oil. After 24 hours, rabbits were euthanized and the aqueous humor (AH) and corneas were removed. The epithelial surfaces of isolated corneas were incubated with 1 ml culture medium (MEM) at room temperature for 1, 4, and 6 hours. Corneal supernatant solutions and AH samples were assayed for the presence of neutrophil chemotactic activity using modified Boyden Chambers.

There were detectable levels of protein content (33.4±3.4 mg/ml), neutrophil chemotactic activity (61±15% fMLF (SEQ ID NO:11)) and neutrophil cell count (17,800±2,400 cells/nm$^3$ in AH samples of endotoxin treated eyes. A high level of chemotactic activity was also detected in corneal supernatants after 1 hr of incubation with release persisting for 4 hr, followed by a decline by 6 hr, presumably due to enzymatic deactivation. The 3 KDa cornea-derived Nourin was identified (93±1.1% f-MLF (SEQ ID NO:11)) in the corneal supernatant solutions. Control eyes, on the other hand, did not show an elevation of cell count or protein content in AH samples. Similarly, there was no release of chemotactic factors from isolated corneas incubated in buffer solution. In conclusion, the 3 KDa Nourin is detected in AH and released by corneal tissues of an endotoxin-Uveitis model of rabbit.

Example 5

Leukocyte Chemotactic Factors Released by Vascular Tissues in Response to Ischemic Injury and Shear Stress (Pressure)

Isolated bovine coronary artery pieces: The release of neutrophil chemotactic factor from vascular tissues was demonstrated using isolated bovine coronary arteries. Coronary arteries were isolated from fresh bovine hearts then cut into pieces and incubated for 1, 2, 3, and 4 hours at room temperature. High levels of chemotactic activity (2-3 fold of the positive control fMLF (SEQ ID NO:11)) was released by the first hour of incubation and continued on for additional three hours (Elgebaly, 1987).

Isolated Canine Vein Grafts: Significant release of neutrophil chemotactic factor was also detected in extended vein grafts of dogs. For these studies, leg veins were isolated and extended under pressure (300 mmHg) for 15 minutes then the inner surfaced allowed to incubate with buffer for an additional 45 minutes. High levels of chemotactic activity (5-7 fold) were detected in the inner buffer solutions isolated from the extended vein grafts compared to the in situ control veins where the blood was removed and replaced with buffer for 1 hour without any extension (Elgebaly, 1990).

Isolated Human Vein Grafts: Patients' leg veins were removed from five patients scheduled for coronary bypass surgery. The samples for each patient were distended for 10 minutes at 300 mm Hg pressure and incubated in buffer (HBSS) for 1 hour at room temperature. Undistended vein grafts were incubated at room temperature in HBSS for one hour and then the solutions were tested for chemotactic activity.

Chemotaxis Assay: The chemotactic activity of vein samples was tested using standard chemotaxis assay. Briefly, neutrophils were isolated from human peripheral blood and labeled by fluorescence dye. These labeled neutrophils were used as migratory cells and placed on the top chamber of the 96 well chemotaxis plates. The vein samples were placed at the bottom wells of the plate. A filter was placed in between and the ability of the tested samples to stimulate the migration of neutrophils across the membrane was determined by incubating the chamber at 37° C. for 1 hour. The standard synthetic chemoattractant f-Met-Leu-Phe (f-MLF (SEQ ID NO:11)) was used as the positive control for 100% chemotactic response. Hank's Balanced Salt Solution (HBSS) was the negative control for random migration. Neutrophil migration was reported as the number of labeled neutrophils detected at the bottom wells which crossed the membrane filter in response to the test solutions. The samples were tested in triplicate wells.

Inhibition of the human vascular Nourin by the N-formyl-methionyl blocker t-Boc-FLFLF (SEQ ID NO:2): t-Boc FLFLF (SEQ ID NO:2) is a FPR antagonist and was tested for its ability to inhibit Nourin activity on neutrophil migration. In the chemotaxis chamber, t-Boc-FLFLF (SEQ ID NO:2) was used at a final concentrations of $10^{-5}$ Molar. Results indicated that that t-Boc-FLFLF (SEQ ID NO:2) at $10^{-5}$ M inhibited up to 60% of neutrophil chemotaxis induced by vascular Nourin. In one human sample, t-Boc-FLFLF (SEQ ID NO:2) inhibited 100% of neutrophil chemotaxis. Similarly, the FPR antagonist Spinorphin inhibited neutrophil chemotaxis stimulated by Nourin.

Results of this human study support that a potent chemotactic factor is rapidly released within 10 minutes by vascular tissues under non-physiological conditions including ischemia and pressure extension. Vascular Nourin, similar to epithelial Nourin, is inhibited by FPR antagonists such as t-Boc-FLFLF (SEQ ID NO:2).

Example 6

Tissue Protection by Cyclocreatine and Reduction of Apoptosis

Cyclocreatine (25 gm in 500 ml saline) was injected intravenously into a dog one hour before the induction of global warm ischemia. Control dogs received saline. All dogs underwent one hour of global warm ischemia by cross clamping the aorta. After the one hour of warm ischemia, hearts were removed, perfused for an additional four hours with buffer containing 1% cyclocreatine (20 gm in 2 liters), and then placed on a working Longerdorff to measure cardiac function. After the initiation of the aortic cross clamping, cyclocreatine-treated heart continued to beat for 9 minutes during warm ischemia, while the control heart stopped beating after 2 minutes. Similarly, myocardial pH was 7.04 in the cyclocreatine-treated heart compared to pH 6.00 in control heart when measured 6 minutes after the induction of warm ischemia.

Biochemical and functional analyses demonstrating the cardioprotection by cyclocreatine treatment are as follows: three-fold increase of myocardial ATP as tissue energy metabolism in cyclocreatine-treated heart compared to controls; significant reduction in apoptosis in cyclocreatine-treated heart compared to controls as measured by caspase enzyme activity; reduced intracellular edema compared to control as measured by MRI; reduced level of the cell injury marker malondialdehyde compared to controls; reduced myocardial tissue lactic acidosis compared to control (per MRI); reduced level of the cardiac-derived leukocyte factor; reduced inflammation/pain and injury induced by inflammation; reduced TNF-α released by monocytes and therefore reduced apoptosis.

The cyclocreatine-treated heart continued to show strong contractility throughout the one-hour analysis on the Longerdorff working heart, while control hearts showed strong contractility only during the first 15-20 minutes then the contractility declined. The results indicated a reduction of the caspase enzyme activities in the cyclocreatine dog (26-76% reduction of baseline) compared to the significant stimulation observed in control dogs (1.44-3.86-fold increase over baseline). Interestingly, the significant reduction of caspase activities indicates that the enzymes may be present more in the "inactive proenzyme" forms. Cyclocreatine treatment may stimulate the anti-apoptotic members of the family such as Bcl-2 and/or Bcl-x, or inhibit the pro-apoptotic members of the family such as Bak, Bax, and Bim.

In general, when cells are injured, the anti-apoptotic Bcl-2 and/or Bcl-x are lost from the mitochondrial membrane and are replaced by the pro-apoptotic Bak, Bax, and Bim. Furthermore, when BCl-2/Bcl-x levels decrease, the permeability of the mitochondrial membrane increases, and several proteins that can activate the caspase cascade leak out. One of these proteins is cytochrome C, well-known for its role in myocardial respiration. In the cytosol, cytochrome C binds to a protein called Apaf-1 (apoptosis activating factor-1), and the complex activates caspase enzymes.

Because apoptosis plays a very important role in the pathogenesis of ischemia-induced tissue failure and loss of function, reducing caspases activities by cyclocreatine in this example helps prevent and treat organ injury in nerve and ocular tissues. Further, because ATP depletion is a major event in ischemic stroke, peripheral nerve ischemia, and retinal damage, preservation of the energy source in such organs can significantly protect the nerve tissues (brain, spinal column, retinal tissues, and optic nerves) from ischemic injury and restore functionality.

Example 7

Role of Leukocyte Chemotactic Factors in the Development of Cytokine Storms

It is known in the art that serum TNF-α concentrations in excess of 1 ng/ml in a patient are frequently predictive of a lethal outcome. As described in Table 1, the tissue-derived LCF Nourin incubated with human monocytes for only 4 hours stimulated the release of significantly high levels of the cytokine storms key inflammatory mediators including TNF-α (400 pg/ml), IL-β (400 pg/ml), and IL-8 (12,000 ng/ml). Monocytes incubated with control media released significantly less chemokines and cytokines. These data further supports a role of the endogenous Nourin as an "early" potent mediator in the pathogenesis of cytokine storms documented to occur secondary to complications of Avian flu infection.

Studies by Tumpey and co-workers (Tumpey et al., 2005) demonstrated the detection of 350 pg/ml TNF-α in lung homogenates of mice infected with the highly pathogenic 1918 influenza virus for 5 days. It is believed that epithelial-derived Nourin released by lung tissue shortly after viral infection is one of the key inflammatory mediators which activate resident lung macrophages and recruited monocytes to release high levels chemokines and cytokines including TNF-α. The early release of Nourin by influenza infected lungs and its key role in evoking the observed cytokine storms can, therefore, be the basis for developing therapeutic products aimed at combating excessive host inflammatory response which kills patients infected by the Avian influenza. Therapeutic compositions of the invention that reduce the levels of the tissue-derived Nourin will also inhibit the levels of several pro-inflammatory mediators including TNF-α and finally protect tissues from TNF-α induced apoptosis.

TABLE 1

LCF Nourin Stimulates the Release of High Levels of Chemokines and Cytokines by Human Peripheral Monocytes

| | Nourin | Control Media |
|---|---|---|
| Interleukin-8 | 12,000 ng/ml | 2,000 ng/ml |
| Interleukin-β | 400 pg/ml | 10 pg/ml |
| Tumor Necrosis Factor-α | 400 pg/ml | <10 pg/ml |

As will be apparent to persons skilled in the art, various modifications, adaptations and variations of the foregoing specific disclosure can be made without departing from the teachings of the present invention as defined in the appended claims.

REFERENCES

Bjornheden et al., *Arterioscler. Thromb. Vasc. Biol.* 19:870-876, 1999.

Clair T. et al., *Lipids in Health and Disease,* 4:5, 2005.

de Paulis J., *Allergy Clin. Immunol.:* 98 (1): 152-64, 1996.

Elgebaly S., *Ocular Pharmacal.* 10(1): 295-305, 1994.

Elgebaly S., *Am. J. Pathol.* 116(3): 407-416, 1984.

Elgebaly S., *Alcohol, Immunomodulation, and AIDS:* 75-78, 1990.

Elgebaly S., Eleventh International Reticuloendothelial Society Meeting, Kawai, Hawaii, 1987.

Feliu E., *Eur. J. Clin. Invest.* 7:571-577, 1977.

Galoyan A., *Neurochem. Res.* 31(6), 795-803, 2006.

Grinberg L., *Mod. Pathol.* 14, 482-495, 2001.

Guo et al., *J. Neuroimmunology,* 131, 160-167, 2002.

Kalns, *J. Biochem. Biophys. Res. Commun.* 297 (3), 506-9, 2002.

Lai et al., *J. Neuroimmunology,* 128, 101-108, 2002.

Nguyen K., *Biochemistry* 42; 9952-9958, 2003.

Prince A., *J. Clin. Inv.* 112, 656-658, 2003.

Rowley, G., *J. Am. Chem. Soc.* 93: 5542-5551, 1971.

Tessier J. et al., *Infect. Immun.*, Jan. 29, 2007.

Tumpey et al., *J. Virology* 79 (23), 14933-14944, 2005.

VanEpps D., *Ann. Intern. Med.* 59:200-207, 1975.

Yamamoto Y. et al., *Current Protein & Peptide Science,* 3, 587-599, 2002.

Yamamoto Y. et al., *Biochemical Pharmacology,* 54, 695-701, 1997.

The invention claimed is:

1. A method of treating target mammalian tissue subject to injury, pain, ischemia, or infectious agents involving the activity of Nourin, said method comprising administering to the mammalian tissue an effective amount of: 1) an anti-apoptotic agent selected from cyclocreatine and cyclocreatine phosphate; and 2) an anti-inflammatory agent selected from cyclosporin H and a soluble formyl peptide receptor;
   wherein both the anti-apoptotic agent and the anti-inflammatory agent inhibit the activity of Nourin.

2. The method of claim 1, wherein the anti-inflammatory agent is cyclosporin H.

3. The method of claim 1, wherein the anti-inflammatory agent is a soluble formyl peptide receptor.

4. The method of claim 1, wherein the anti-apoptotic agent is cyclocreatine.

5. The method of claim 1, wherein the anti-apoptotic agent is cyclocreatine phosphate.

6. The method of claim 1, wherein the anti-inflammatory agent and the anti-apoptotic agent are administered prophylactically prior to injury.

7. The method of claim 1, wherein the anti-inflammatory agent and the anti-apoptotic agent are administered therapeutically during injury or post-injury.

8. The method of claim 1, wherein the anti-inflammatory agent and the anti-apoptotic agent are administered to the mammal from which the mammalian tissue derives by injection, oral administration, topical administration, or by inhalation.

9. The method of claim 1, wherein the mammalian tissue is human tissue.

10. The method of claim 1, wherein said method further comprises:
    taking a sample of the target mammalian tissue;
    detecting the release of at least Nourin from the target mammalian tissue, wherein the release of the at least one protein indicates that the mammalian tissue is in an injured state; and
    if the tissue is in an injured state, administering to the mammal from which the tissue derives an effective amount of the anti-apoptotic agent and the anti-inflammatory agent.

11. The method of claim 1, which is a method of treating mammalian tissue subject to injury due to apoptotic cell death as a result of the activity of Nourin, said method comprising the step of administering to the mammal from which the tissue derives: 1) cyclocreatine or cyclocreatine phosphate in an amount between 0.03 g and 0.08 g per kg of mammal body weight, and 2) cyclosporin H or a soluble formyl peptide receptor.

12. The method of claim 11, wherein the treatment reduces or eliminates apoptosis in the injured tissue.

13. The method of claim 1, wherein the soluble formyl peptide receptor comprises the sequence of SEQ ID NO:12.

* * * * *

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide
```

```
<400> SEQUENCE: 1

Met Ile Ile Asn His Asn Leu Ala Ala Ile Asn Ser His
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Phe Leu Phe Leu Phe
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Leu Val Val Tyr Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Val Val Tyr Pro Trp
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic peptide

<400> SEQUENCE: 5

Met Leu Phe
1

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Arg Pro Lys Pro Phe Gln Trp Phe Trp Leu Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7
```

```
Arg Pro Pro Gly Phe Ser Pro Phe Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Pro Pro Gly Phe Ser Pro Phe Arg
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Arg Pro Lys Pro Gln Gln Phe Phe Gly Leu Met
1               5                   10

<210> SEQ ID NO 10
<211> LENGTH: 2
<212> TYPE: PRT
<213> ORGANISM: Artificial Sequence
<220> FEATURE:
<223> OTHER INFORMATION: Synthetic peptide

<400> SEQUENCE: 10

Phe Met
1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide

<400> SEQUENCE: 11

Met Leu Phe
1

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Arg Lys Ala Met Gly Gly His Trp Pro Phe Gly Trp Phe Leu Cys Lys
1               5                   10                  15

Phe
```